(12) United States Patent
Bosch et al.

(10) Patent No.: US 11,320,433 B2
(45) Date of Patent: May 3, 2022

(54) ANTI-DENGUE VIRUS NS1 PROTEIN MONOCLONAL ANTIBODIES

(71) Applicants: Massachusetts Institute of Technology, Cambridge, MA (US); The United States of America as Represented by the Secretary of the Department of Health and Human Services, Silver Spring, MD (US)

(72) Inventors: Irene Bosch, Brookline, MA (US); Kimberly Hamad-Schifferli, Somerville, MA (US); Jose Gomez-Marquez, Cambridge, MA (US); Helena dePuig Guixe, Cambridge, MA (US); Lee Gehrke, Cotuit, MA (US)

(73) Assignees: Massachusetts Institute of Technology, Cambridge, MA (US); The United States of America as Represented by the Secretary of the Department of Health and Human Services, Silver Springs, MD (US)

( * ) Notice: Subject to any disclaimer, the term of this patent is extended or adjusted under 35 U.S.C. 154(b) by 210 days.

(21) Appl. No.: 16/707,508

(22) Filed: Dec. 9, 2019

(65) Prior Publication Data
US 2020/0363415 A1 Nov. 19, 2020

Related U.S. Application Data

(62) Division of application No. 15/429,756, filed on Feb. 10, 2017, now Pat. No. 10,551,381.

(60) Provisional application No. 62/293,990, filed on Feb. 11, 2016.

(51) Int. Cl.
*G01N 33/569* (2006.01)
*C07K 16/10* (2006.01)

(52) U.S. Cl.
CPC ... *G01N 33/56983* (2013.01); *C07K 16/1081* (2013.01); *C07K 2317/34* (2013.01); *C07K 2317/92* (2013.01); *G01N 2333/08* (2013.01); *G01N 2469/10* (2013.01); *Y02A 50/30* (2018.01)

(58) Field of Classification Search
None
See application file for complete search history.

(56) References Cited

U.S. PATENT DOCUMENTS

| | | |
|---|---|---|
| 5,104,812 A | 4/1992 | Kurn et al. |
| 5,731,162 A | 3/1998 | Gatti et al. |
| 5,853,670 A | 12/1998 | Bunce |
| 6,596,476 B1 | 7/2003 | Lesniewski et al. |
| 6,870,032 B1 | 3/2005 | Flamand et al. |
| 7,622,113 B2 | 11/2009 | Lai et al. |
| 8,263,418 B2 | 9/2012 | Brennan et al. |
| 8,920,804 B2 | 12/2014 | Raychaudhuri et al. |
| 2002/0127737 A1 | 9/2002 | Degelaen et al. |
| 2004/0014094 A1 | 1/2004 | Lee et al. |
| 2005/0250141 A1 | 11/2005 | Lambert et al. |
| 2008/0176263 A1 | 7/2008 | Schultz et al. |
| 2010/0233708 A1 | 9/2010 | Mehra et al. |
| 2010/0279400 A1 | 11/2010 | Wong et al. |
| 2012/0014945 A1 | 1/2012 | Wu et al. |
| 2013/0157351 A1 | 6/2013 | Ozcan et al. |
| 2013/0280698 A1 | 10/2013 | Propper et al. |
| 2014/0045727 A1 | 2/2014 | Yin et al. |
| 2014/0056913 A1 | 2/2014 | Sasisekharan et al. |
| 2014/0170642 A1 | 6/2014 | Huang et al. |

(Continued)

FOREIGN PATENT DOCUMENTS

| | | |
|---|---|---|
| CN | 101226196 A | 7/2008 |
| CN | 101551393 A | 10/2009 |

(Continued)

OTHER PUBLICATIONS

Chen, Y. et al., "Comprehensive Mapping of Immunodominanyt and Conserved Serotype-and-Group-Specific B-Cell Epitopes of Nonstructiral Protein 1 from Dengue Virus Type 1", Virology, 398(2), Mar. 15, 2010, 290-298.

(Continued)

*Primary Examiner* — Agnieszka Boesen
(74) *Attorney, Agent, or Firm* — Elmore Patent Law Group, P.C.; Mahreen Chaudhry Hoda; Carolyn S. Elmore

(57) ABSTRACT

The present invention provides matched antibody pairs for the specific detection of one or more of the four dengue virus serotypes in a biological sample that may contain one or more of such dengue virus serotypes. Each matched antibody pair is capable of detecting not more than one serotype of dengue virus NS1 protein that may be present in the sample and will not cross react with other serotypes that may be present in the sample. Multiple matched pairs may be used to detect one or more dengue virus serotypes that may be present in a sample. Such matched pair antibodies, facilitate the development of confirmatory in vitro diagnostic tests such as sandwich immunoassays, that detect and distinguish the presence of one or more dengue virus serotypes in a biological sample, preferably a sample derived from human subject. The invention also provides kits comprising the matched antibody pairs of the invention and methods for using the kits for immunoassays for the specific detection of one or more serotypes of dengue virus in a patient population. The present invention also provides monoclonal antibodies specific for the NS1 protein of dengue virus and therapeutic compositions and methods for treating dengue virus infection.

7 Claims, 26 Drawing Sheets
Specification includes a Sequence Listing.

(56) References Cited

U.S. PATENT DOCUMENTS

| | | |
|---|---|---|
| 2014/0171891 A1 | 6/2014 | Lopez et al. |
| 2014/0206100 A1 | 7/2014 | Saul |
| 2014/0356864 A1 | 12/2014 | Khan |
| 2015/0054546 A1 | 2/2015 | Redgrave |
| 2015/0056687 A1 | 2/2015 | Tyrrell et al. |
| 2015/0293085 A1 | 10/2015 | Anderberg et al. |

FOREIGN PATENT DOCUMENTS

| | | |
|---|---|---|
| CN | 101576560 A | 11/2009 |
| CN | 101726593 A | 6/2010 |
| FR | 2974907 A1 | 11/2012 |
| WO | 2012153031 A1 | 11/2012 |
| WO | 2014070935 A1 | 5/2014 |
| WO | 2014080212 A2 | 5/2014 |
| WO | 2014171891 A1 | 10/2014 |
| WO | 2015054546 A1 | 4/2015 |

OTHER PUBLICATIONS

Cockburn, J. B. et al., "Mechanism of Dengue Virus Broad Cross-Neutralization by a Monoclonal Antibody", Structure, 20(2), Jan. 2, 2012, 303-314.

Eltzov, E. et al., "Lateral Flow Immunoassays-from Paper Strip to Smartphone Technology", Electroanalysis vol. 27, 2015, pp. 1-16.

Gao, X. et al., "Recent Advances in Nanoparticles-Based Lateral Flow Biosensors", American Journal of Biomedical Sciences, 6(1), 2014, 41-57.

Grimes, J. M. et al., "Enhancement of Lateral Flow Assay for the Detection of Whole Viral Particle and Chlamydial Elementary Bodies", Masters Thesis, University of Massachusetts—Amherst, Paper 1182, Feb. 2014.

Hu, R. , "Metallic Nanostructures as Localized Plasmon Resonance Enhanced Scattering Probes for Multiplex Dark Field Targeted Imaging of Cancer Cells", J. Phys. Chern Nanometer Interfaces 113(7), 2009, 2676-2684.

Sajid, M. et al., "Designs, Formats and Applications of Lateral Flow Assay: A Literature Review", Journal of Saudi Chemical Society, 2014, pp. 1-17.

Taranova, N. A. et al., "Traffic Light Immunochromatographic Test Based on Multicolor Quantum Dots for the Simultaneous Detection of Several Antibiotics in Milk", Biosensors and Bioelectronics, vol. 63, 2015, 255-261.

Yen, C-W et al., "Multicolored Silver Nanoparticles for Multiplexed Disease Diagnostics Distinguishing Dengue, Yellow Fever, and Ebola Viruses", Lab on a Chip, 15(7), Jan. 1, 2015, 1638-1641.

Alere, SD BIOLINE Dengue RDT Series, Standard Diagnostics, INC., 4 pages, 2013.

Colman, P. , "Effects of amino acid sequence changes on antibody-antigen interactions", Research in Immunology, vol. 145, No. 1, 1994, 33-36.

Harlow, E. et al., "Antibodies A laboratory Manual", Cold Spring Harbor Laboratory, 1988, 25-26, 37-59.

Lederman, S. et al., "A Single Amino Acid Substitution in a Common African Allele of the CD4 Molecule Ablates Binding of the Monoclonal Antibody, OKT4", Mol. Immunol., vol. 28, No. 11, Nov. 28, 1991, 1171-1181.

Wang, S. et al., "Early Diagnosis of Dengue Infection Using a Commercial Dengue Duo Rapid Test Kit for the Detection of NS1, IGM, and IGG", Am. J. Trap. Med. Hyg., vol. 83, No. 3, 2010, 690-695.

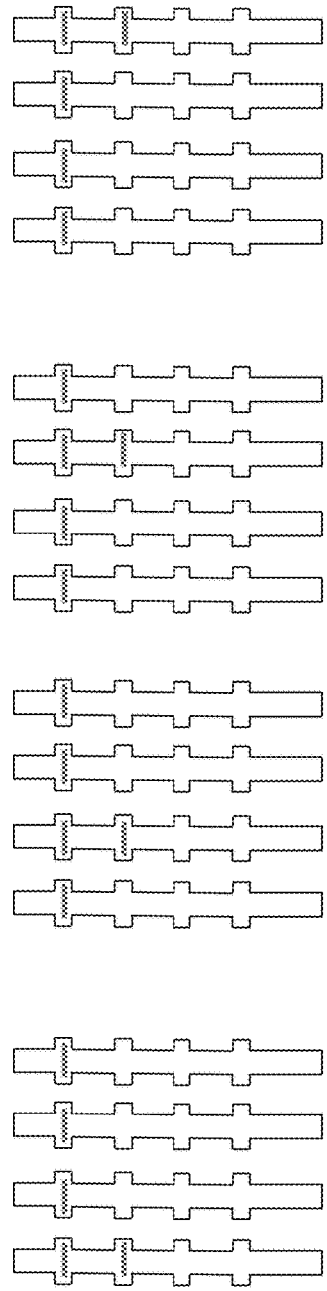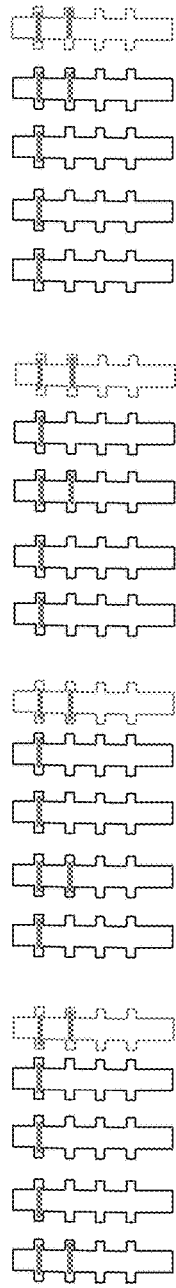
FIG. 1

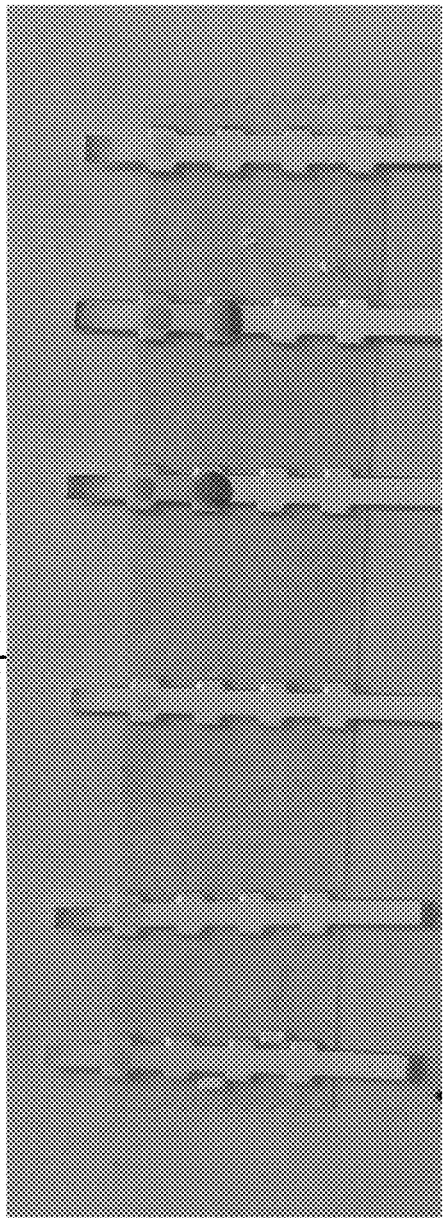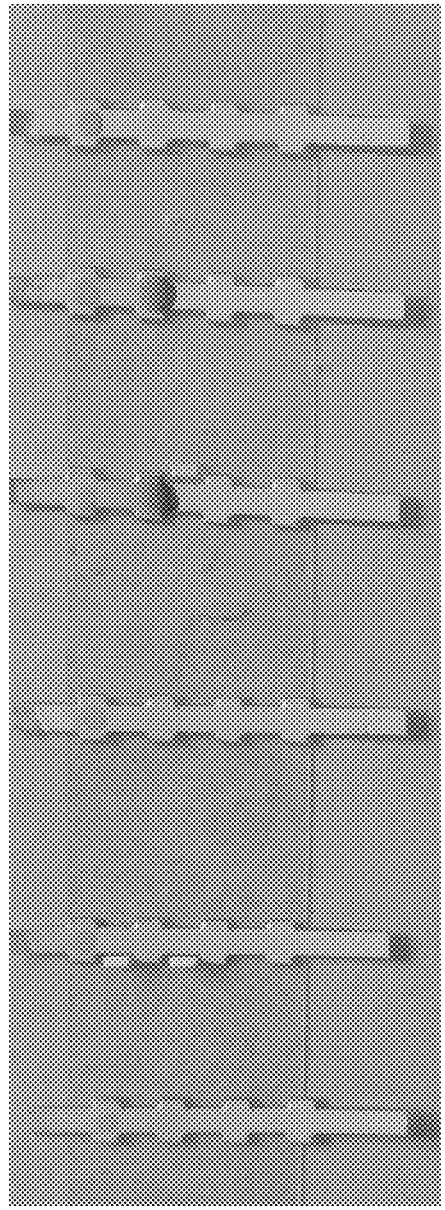
FIG. 3

(Reversible)

Summary of peptide sequences recognized by each antibody

Ab 323

DV4: PVNDLKYSWKTWGKAKI (SEQ ID NO: 1) +++ (peptide 20)

DV3: MELKYSWKTWGLAKIVT (SEQ ID NO: 2) +++ (peptide 20)

DV3: GVFTTNIWLKLREVYTQ (SEQ ID NO: 3) ++ (peptide 29)

Ab 55

DV3: GVFTTNIWLKLREVYTQ (SEQ ID NO: 3) + (peptide 29)

DV3: VEDYGFGVFTTNIWLKL (SEQ ID NO: 4) + (peptide 28)

DV3: MELKYSWKTWGLAKIVT (SEQ ID NO: 2) ++ (peptide 20)
DV4: GFGMFTTNIWMKFREG ++ (peptide 29) (SEQ ID NO: 5)

Ab 626

DV3: MELKYSWKTWGLAKIVT (SEQ ID NO: 2) ++ (peptide 20)

DV4: CRSCTMPPLRFLGEDG (SEQ ID NO: 6) + (peptide 56)
DV4: MPPLRFLGEDGCWYGME (SEQ ID NO: 7) + (peptide 57)
DV4: GFGMFTTNIWMKFREG (SEQ ID NO: 5) ++ (peptide 29)

Ab 411

DV3: MELKYSWKTWGLAKIVT (SEQ ID NO: 2) ++ (peptide 20)
DV4: nothing

Ab 271

DV3: MELKYSWKTWGLAKIVT (SEQ ID NO: 2) ++ (peptide 20)

DV3: GVFTTNIWLKLREVYTQ (SEQ ID NO: 3) + (peptide 29)

FIG. 10

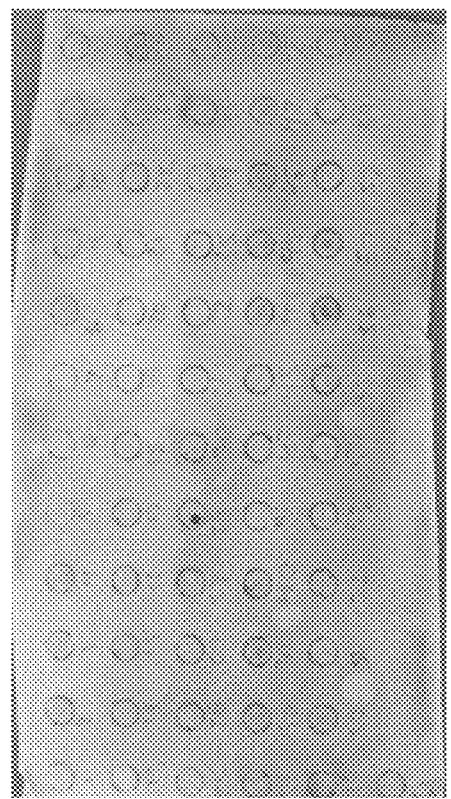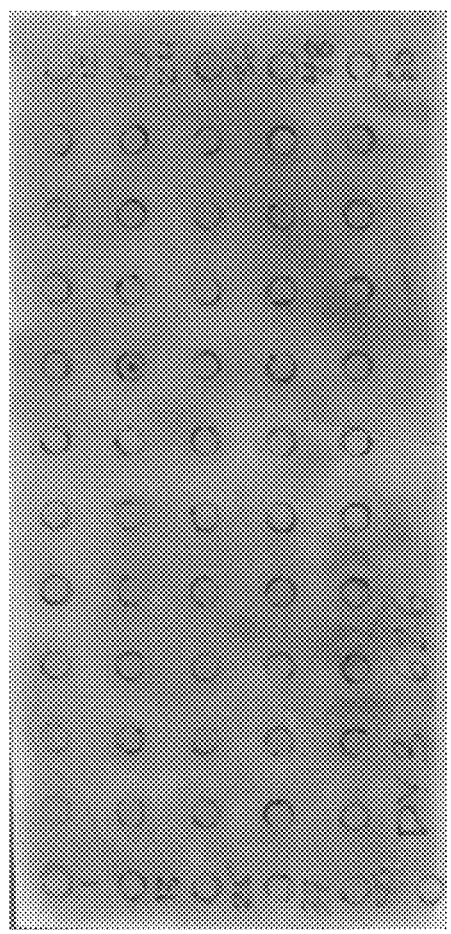
FIG. 14

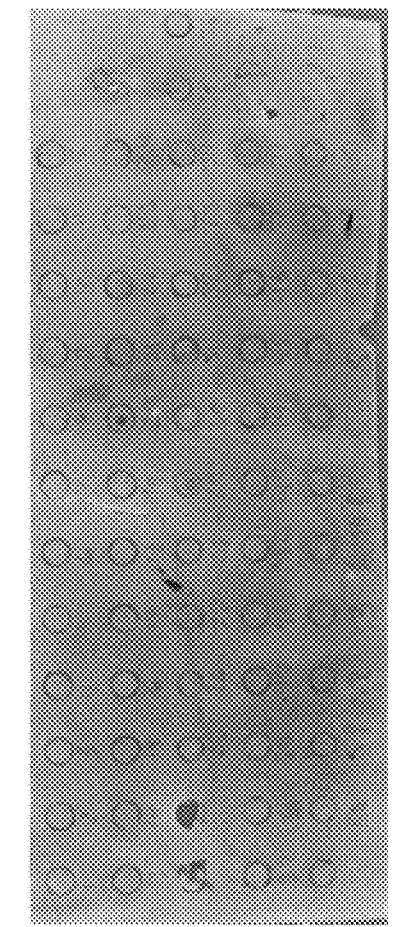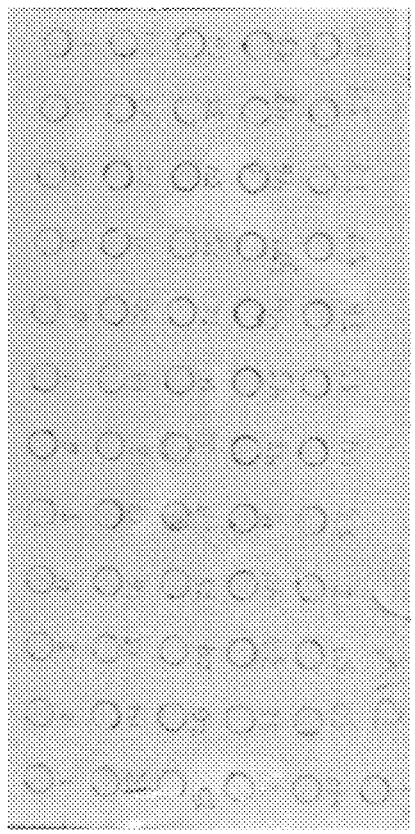
FIG. 15

Approximate location of peptides 20 and 29

Antibody 55 Heavy chain: DNA sequence (411 bp)
Leader sequence-FR1-CDR1-FR2-CDR2-FR3-CDR3-FR4
ATGAAATGCAGCTGGGTTATCTTCTTCCTGATGGCAGTGGTTACAGGGGTCAATTCAGAGGTTC
AGCTGCATCAGTCTGGGGCAGAGCTTGTGAAGCCAGGGGCCTCAGTCAAGTTGTCCTGCACAGT
TTCTGGCTTCAACATTAAAGACACCTATATTCACTGGGTGAAACAGAGGCCTGAACAGGGCCTG
GAGTGGATTGGAAGGATTGATCCTGCAAATGGTAATACTGAATATGACCCGAAGTTCCAGGGCA
AGGCCACTATAAAAGCCGACACTTCCTCCAACACAGCCTACCTGCAACTCATCAGTCTGACATC
TGAGGACACTGCCGTCTATTACTGTGCTTTTTATTACTACGGTCGTAGCCTTGCTTACTGGGGC
CAAGGGACTCTGGTCACTGTCTCTGCA (SEQ ID NO: 8)

Antibody 55 Heavy chain: Amino acids sequence (137 AA)
Leader sequence-FR1-CDR1-FR2-CDR2-FR3-CDR3-FR4
MKCSWVIFFLMAVVTGVNSEVQLHQSGAELVKPGASVKLSCTVSGFNIKDTYIHWVKQRPEQGL
EWIGRIDPANGNTEYDPKFQGKATIKADTSSNTAYLQLISLTSEDTAVYYCAFYYYGRSLAYWG
QGTLVTVSA (SEQ ID NO: 9)

Antibody 55 Light chain: DNA sequence (381 bp)
Leader sequence-FR1-CDR1-FR2-CDR2-FR3-CDR3-FR4
ATGAGTGTGCCCACTCAGGTCCTGGGGTTGCTGCTGCTGTGGCTTACAGATGCCAGATGTGACA
TCCAGATGACTCAGTCTCCAGCCTCCCTATCTGTGTCTGTGGGAGAAACTGTCACCATCACATG
TCGAACAAGTGAGAATATTTACAGTAGTTTAGCATGGTATCAGCAGAAACAGGGAAAATCTCCT
CAGCTCCTGGTCTATGCTGCAGCTAACTTAGCGGATGGTGTGCCATCAAGGTTCAGTGGCAGTG
GATCAGGCACACAGTATTCCCTCAAGATCAACAGCCTGCAGTCTGAAGATTTTGGAACTTATTA
CTGTCAACATTTTGGGGTACTCCGTGGACGTTCGGTGGAGGCACCAAGCTGGAAATCAAA
(SEQ ID NO: 10)

Antibody 55-Antibody Light chain: Amino acids sequence (127 AA)
Leader sequence-FR1-CDR1-FR2-CDR2-FR3-CDR3-FR4
MSVPTQVLGLLLLWLTDARCDIQMTQSPASLSVSGETVTITCRTSENIYSSLAWYQQKQGKSP
QLLVYAAANLADGVPSRFSGSGSGTQYSLKINSLQSEDFGTYYCQHFWGTPWTFGGGTKLEIK
(SEQ ID NO: 11)

FIG. 18

Antibody 271 Heavy chain: DNA sequence (408 bp)
Leader sequence-FR1-CDR1-FR2-CDR2-FR3-CDR3-FR4
ATGAAATGCAGCTGGGTCATCTTCTTCCTGATGGCAGTGGTTACAGGGGTCAATTCAGAGGTTC
AGCTGCAGCAGTCTGGGGCTGAGCTTGTGAGGCCAGGGGCCTTAGTCAAGTTGTCCTGCAGAGC
TTCTGGCTTCAGAATTAGAGACTACTATATACACTGGGTGAAGCAGAGGCCTGAACAGGGCCTG
GAGTGGATTGGATGGATTGATCCTGAGTATGGTAATACTATTTATGACCCGAACTTCCGGGGCA
AGGCCAGTATAACATCAGACACATCCTCCAACACAGCCTACCTGCAGCTCAGCAGCCTGTCTTC
TGAGGACACAGCCGTCTATTACTGTGCCTCGTATTATTACGGTGGTGTGAACTACTGGGGCCAA
GGCACCACTCTCACAGTCTCCTCA (SEQ ID NO: 12)

Antibody 271 Heavy chain: Amino acids sequence (136 AA)
Leader sequence-FR1-CDR1-FR2-CDR2-FR3-CDR3-FR4
MKCSWVIFFLMAVVTGVNSEVQLQQSGAELVRPGALVKLSCRASGFRIRDYYIHWVKQRPEQGL
EWIGWIDPEYGNTIYDPNFRGKASITSDTSSNTAYLQLSSLSSEDTAVYYCASYYYGGVNYWGQ
GTTLTVSS (SEQ ID NO: 13)

Antibody 271 Light chain: DNA sequence (384 bp)
Leader sequence-FR1-CDR1-FR2-CDR2-FR3-CDR3-FR4
ATGGATTTTCAAGTGCAGATTTTCAGCTTCCTGCTAATCAGTGCCTCAGTCATACTGTCCAGAG
GACAAATTGTTCTCACCCAGTCTCCAGCAATCATGTCTGCATCTCCAGGGGAGAAGGTCACCAT
GACCTGCAGTGCCAGTTCAAGTGTAAGTCGCATTTACTGGTACCAGGAGAAGCCAGGATCCTCC
CCCAGACTCCTGATTTATGACACATCCAACCTGGCTTCTGGAGTCCCTGTTCGCTTCAGTGGCA
GTGGGTCTGGGACCTCTTACTCTCTCACAATCAGCCGAATGGAGGCTGAAGATGCTGCCACTTA
TTACTGCCAGCAGTGGAGTAGTTACCCACGGACGTTCGGTGGAGGCACCAAGCTGGAAATCAAA
(SEQ ID NO: 14)

Antibody 271 Light chain: Amino acids sequence (128 AA)
Leader sequence-FR1-CDR1-FR2-CDR2-FR3-CDR3-FR4
MDFQVQIFSFLLISASVILSRGQIVLTQSPAIMSASPGEKVTMTCSASSSVSRIYWYQEKPGSS
PRLLIYDTSNLASGVPVRFSGSGSGTSYSLTISRMEAEDAATYYCQQWSSYPRTFGGGTKLEIK
(SEQ ID NO: 15)

FIG. 19

Antibody 323-Heavy chain: DNA sequence (390 bp)
Leader sequence-FR1-CDR1-FR2-CDR2-FR3-CDR3-FR4
ATGGAATGTAACTGGATACTTCCTTTTATTCTGTCAGTAACTTCAGGTGTCTACTCACAGGTGC
AGCTCCAGCAGTCTGGGACTGAGCTGGCAAGACCTGGGGCTTCAGTGAAATTGTCCTGTAAGGC
TTCTGGCTACACCTTTACTAATTACTGGATACAGTGGGTAAAACAGAGGCCTGGACAGGGTCTG
GAATGGATTGGGGATATTTATCCTGGAGATGGTGATACTAGGTACACTCAGAAGTTCAGGGGCA
AGGCCATATTGACTGCAGATAAATCCTCCAGCACAGCCTATATGGAACTCAGCAGTTTGGCATC
TGAGGACTCTGCGGTCTATTACTGTGCCTCACTAACCTGGGGCCAAGGCACCACTCTCACAGTC
TCCACA (SEQ ID NO: 16).

Antibody 323- Heavy chain: Amino acids sequence (130 AA)
Leader sequence-FR1-CDR1-FR2-CDR2-FR3-CDR3-FR4
MECNWILPFILSVTSGVYSQVQLQQSGTELARPGASVKLSCKASGYTFTNYWIQWVKQRPGQGL
EWIGDIYPGDGDTRYTQKFRGKAILTADKSSSTAYMELSSLASEDSAVYYCASLTWGQGTTLTV
ST (SEQ ID NO: 17).

Antibody 323-Light chain: DNA sequence (399 bp)
Leader sequence-FR1-CDR1-FR2-CDR2-FR3-CDR3-FR4
ATGGAATCACAGACTCAGGTCCTCATGTCCCTGCTGTTCTGGGTATCTGGTACCTGTGGGGACA
TTGTGATGACACAGTCTCCATCCTCCCTGACTGTGACAGCAGGAGAGAAGGTCACTATGAGCTG
CAGGTCCAGTCAGAGTCTGTTAAACAGTGGAAATCAAAAGAACTACTTGACCTGGTACCAGCAG
AGACCAGGGCAGCCTCCTAAACTGCTGATCTACTGGGCATCCACTAGGGAATCTGGGGTCCCTG
ATCGCTTCACAGGCAGTGGATCTGGAACAGATTTCATTCTCACCATCAGCAGTGTGCAGGCTGA
AGACCTGGCAGTTTATTACTGTCAGAATGAGTATAGTTATCCGCTCACGTTCGGTGCTGGGACC
AAGCTGGAGCTGAAA (SEQ ID NO: 18).

Antibody 323- Light chain: Amino acids sequence (133 AA)
Leader sequence-FR1-CDR1-FR2-CDR2-FR3-CDR3-FR4
MESQTQVLMSLLFWVSGTCGDIVMTQSPSSLTVTAGEKVTMSCRSSQSLLNSGNQKNYLTWYQQ
RPGQPPKLLIYWASTRESGVPDRFTGSGSGTDFILTISSVQAEDLAVYYCQNEYSYPLTFGAGT
KLELK (SEQ ID NO: 19).

FIG. 20

Antibody 411- Heavy chain: DNA sequence (408 bp)
Leader sequence-FR1-CDR1-FR2-CDR2-FR3-CDR3-FR4
ATGAAATGCAGCTGGGTCATCTTCTTCCTGATGGCAGTGGTTACAGGGGTCAACTCAGAGGTTC
AGCTGCAGCAGTCTGGGGCTGAGTTTATGAGGCCAGGGGCCTTAGTCAAGTTGTCCTGCAAAGC
TTCTGGCTTCAACATTAAAGACTACTATATGCATTGGGTGAAACAGAGGCCTGAACAGGGCCTG
GAGTGGATTGGATGGATTGACCCTGAGAATGGTAATACTATATATGACCCGAAGTTCCAGGGCA
AGGCCAGTATAACAGCAGACACATCCTCCAACACAGCCTACCTGCAGCTCAGCAGCCTGACTTC
TGAGGACACTGCCGTCTATTACTGTGCCTCGTATTACTACGGTGGTGTGAACTACTGGGGCCAA
GGCACCACTCTCACAGTCTCCTCA (SEQ ID NO: 20)

Antibody 411- Heavy chain: Amino acids sequence (136 AA)
Leader sequence-FR1-CDR1-FR2-CDR2-FR3-CDR3-FR4
MKCSWVIFFLMAVVTGVNSEVQLQQSGAEFMRPGALVKLSCKASGFNIKDYYMHWVKQRPEQGL
EWIGWIDPENGNTIYDPKFQGKASITADTSSNTAYLQLSSLTSEDTAVYYCASYYYGGVNYWGQ
GTTLTVSS (SEQ ID NO: 21)

Antibody 411- Light chain: DNA sequence (384 bp)
Leader sequence-FR1-CDR1-FR2-CDR2-FR3-CDR3-FR4
ATGGATTTTCAAGTGCAGATTTTCAGCTTCCTGCTAATCAGTGCCTCAGTCATTCTGTCCAGAG
GACAAATTGTTCTCACCCAGTCTCCAGCAATCATGTCTGCATCTCCAGGGGAGAAGGTCACCAT
GACCTGCAGTGCCAGCTCAACTGTAAGTTCCATTTACTGGTTCCAGCAGAGGCCAGGATCCTCC
CCCAGACTCCTGATTTATGACACATCCAAACTGGCTTCTGGAGTCCCTATTCGCTTCACTGGCA
GTGGGTCTGGGACCTCTTACTCTCTCACAATCAGCCGAATGGGGGCTGAAGATGCTGCCACTTA
TTACTGCCAGCAGTGGAGTAGTTACCCACGGACGTTCGGTGGAGGCACCAAGCTGGAAATCAAA
(SEQ ID NO: 22)

Antibody 411- Light chain: Amino acids sequence (128 AA)
Leader sequence-FR1-CDR1-FR2-CDR2-FR3-CDR3-FR4
MDFQVQIFSFLLISASVILSRGQIVLTQSPAIMSASPGEKVTMTCSASSTVSSIYWFQQRPGSS
PRLLIYDTSKLASGVPIRFTGSGSGTSYSLTISRMGAEDAATYYCQQWSSYPRTFGGGTKLEIK
(SEQ ID NO: 23)

FIG. 21

Antibody 626-Heavy chain: DNA sequence (414 bp)
Leader sequence-FR1-CDR1-FR2-CDR2-FR3-CDR3-FR4
ATGGCTGTCCTGGTGCTGTTCCTCTGCCTGGTTGCATTTCCAAGCTGTGTCCTGTCCCAGGTGC
AGCTGAAGGAGTCAGGACCTGGCCTGGTGGCGCCCTCACAGAGCCTGTCCATCACTTGCACTGT
CTCTGGGTTTTCATTAACCAGCTATGGTGTACACTGGGTTCGCCAGCCTCCAGGAAAGGGTCTG
GAGTGGCTGGGAGTAATATGGCCTGGTGGAAGCACAAATTATAATTCGGCTCTCATGTCCAGAC
TGAGCATCAGCAAAGACAGTTCCAAGAGCCAAGTTTTCTTAAAAATGAACAGTCTGCAACCTGA
TGACACAGCCATATACTACTGTGCCAGAGAGCCGATCTACGGTAGTAGGTACTTCGATGTCTGG
GGCGCAGGGACCACGGTCACCGTCTCCTCA (SEQ ID NO: 24)

Antibody 626- Heavy chain: Amino acids sequence (138 AA)
Leader sequence-FR1-CDR1-FR2-CDR2-FR3-CDR3-FR4
MAVLVLFLCLVAFPSCVLSQVQLKESGPGLVAPSQSLSITCTVSGFSLTSYGVHWVRQPPGKGL
EWLGVIWPGGSTNYNSALMSRLSISKDSSKSQVFLKMNSLQPDDTAIYYCAREPIYGSRYFDVW
GAGTTVTVSS (SEQ ID NO: 25)

Antibody 626-Light chain: DNA sequence (381 bp)
Leader sequence-FR1-CDR1-FR2-CDR2-FR3-CDR3-FR4
ATGGTATCCACACCTCAGTTCCTTGTATTTTTGCTTTTCTGGATTCCAGCCTCCAGAGGTGACA
TCCTGCTGACTCAGTCTCCAGCCATCCTGTCTGTGAGTCCAGGAGAAAGAGTCACTCTCTCCTG
CAGGGCCAGTCAGAGCATTGGCACAAGAATACACTGGTATCAGCAAAGAACAAATGGTTCTCCA
AGGCTTCTCATAAAGTTTGCTTTTGAGTCTATCTCTGGGATCCCTTCCAGGTTTAGTGGCAGTG
GATCAGGGACAGATTTTACTCTTAGCATCAACAGTGTGGAGTCTGAAGATATTGCAGAGTATTA
CTGTCAACAGAGTATTAACTGGCCGCTCACGTTCGGTGCTGGGACCAAGCTGGAACTGAAA
(SEQ ID NO: 26)

Antibody 626- Light chain: Amino acids sequence (127 AA)
Leader sequence-FR1-CDR1-FR2-CDR2-FR3-CDR3-FR4
MVSTPQFLVFLLFWIPASRGDILLTQSPAILSVSPGERVTLSCRASQSIGTRIHWYQQRTNGSP
RLLIKFAFESISGIPSRFSGSGSGTDFTLSINSVESEDIAEYYCQQSINWPLTFGAGTKLELK
(SEQ ID NO: 27)

FIG. 22

```
DV1  -----DSGCV NKG EL CG G F  T VHTWT QYK QA SPK  SAA  45
DV2  VMVQADSGCV S KN EL CG G F  T VHTWT QYK QP SPS  ASA  50
DV3  -----DMGCV N KG EL CG G F  T VHTWT QYK QA SPK  ATA  45
DV4  -----DMGCV S SG EL CG G F  A VHTWT QYK QP SPA  ASA  45

DV1  GKAWE G CGIRSA RLEN MWKQ SNELNH LLENDMKFT VVGD VG   95
DV2  QKAHE G CGIRSV RLEN MWKQ TPELNH LSENEVKLT MTGD KG  100
DV3  AGAWE G CGIRST RMEN LWKQ ANELNY LWENDIKLT VVGD TG   95
DV4  LNAHK G CGIRST RLEN MWKQ TNELNY LWGGHDLT VAGD KG   95

DV1  ILAQ GKKM RPQPM HKYSWKSWGKAKIIGADIQ NT F  DGPDTPECPD 145
DV2  IMQA GKRS QPQPT LKYSWKTWGKAKMLSTESHNQ F  DGPETAECPN 150
DV3  VLEQ GKRT TPQPM LKYSWKTWGLAKIVTAETQNS F  DGPSTPECPS 145
DV4  VLTK GKRA TPPVN LKYSWKTWGKAKIFTPEARNS F  DGPDTSECPN 145

DV1  DQRAWNIWE VEDYGFGI FTTN WLKLR SYTQMCDHR MSAA KDSKA H 195
DV2  TNRAWNSLE VEDYGFGV FTTN WLKLR KQDVFCDSK MSAA KDNRA H 200
DV3  ASRAWNVWE VEDYGFGV FTTN WLKLR VYTQLCDHR MSAA KDERA H 195
DV4  ERRAWNFLE VEDYGFG  FTTN  YKF GSSEVCDHR MSAA KDQKA H 195

DV1  ADMGYWIES EKNE WK A ASFIEVK CVWPK HTLW GVLES M IPK 245
DV2  ADMGYWIES ALND WK E ASFIEVK CHWPK HTLW GVLES M IPK 250
DV3  ADMGYWIES QKNG WK E ASLIEVK CTWPK HTLW GVLES M IPK 245
DV4  ADMGYWIES SKNQ WQ E ASLIEVK CLWPK HTLW GVLES M IPK 245

DV1  I           RPGYF TQTAGPWH LGK LELDFDLCEGTT VV DEHCGNRG 295
DV2  NF GPVSQHNYRPGYH TQTAGPWH LGK LEMDFDFCEGTT VV TEDCGNRG 300
DV3  SL GPISQHNHRPGYH TQTAGPWH LGK LELDFNYCEGTT VV SENCGTRG 295
DV4  SY GPFSQHNYRQGYA TQTVGPWH LGK LEIDFGECPGTT VT QEDCDHRG 295

DV1  PSLR TT  G   H WCCR CT PPL       CWYGMEIRP VKEKEENL 345
DV2  PSLR TT  G   T WCCRSCTLPPLR R EDGCWYGMEIRP LKEKEENL 350
DV3  PSLR TT  G   H WCCRSCTLPPLR M EDGCWYGMEIRP INEKEENM 345
DV4  PSLR TT  G   T WCCR CT PPL       CWYGMEIRP LSEKEENM 345

DV1  VKSM  AG--- 353 (SEQ ID NO: 29)
DV2  VNSL  A---- 357 (SEQ ID NO: 30)
DV3  VKSL  AG--- 353 (SEQ ID NO: 31)
DV4  VKSQ  AG--- 353 (SEQ ID NO: 32)

mAbs323;1              peptide BEI 20 29
```

FIG. 27

SEQUENCE LISTING

<160> NUMBER OF SEQ ID NOS: 37

<210> SEQ ID NO 1
<211> LENGTH: 17
<212> TYPE: PRT

<213> ORGANISM: Dengue virus 4

<400> SEQUENCE: 1

Pro Val Asn Asp Leu Lys Tyr Ser Trp Lys Thr Trp Gly Lys Ala Lys
1 5 10 15

Ile

<210> SEQ ID NO 2
<211> LENGTH: 17
<212> TYPE: PRT
<213> ORGANISM: Dengue virus 3

<400> SEQUENCE: 2

Met Glu Leu Lys Tyr Ser Trp Lys Thr Trp Gly Leu Ala Lys Ile Val
1 5 10 15

Thr

<210> SEQ ID NO 3
<211> LENGTH: 17
<212> TYPE: PRT
<213> ORGANISM: Dengue virus 3

<400> SEQUENCE: 3

Gly Val Phe Thr Thr Asn Ile Trp Leu Lys Leu Arg Glu Val Tyr Thr
1 5 10 15

Gln

<210> SEQ ID NO 4
<211> LENGTH: 17
<212> TYPE: PRT
<213> ORGANISM: Dengue virus 3

<400> SEQUENCE: 4

Val Glu Asp Tyr Gly Phe Gly Val Phe Thr Thr Asn Ile Trp Leu Lys
1 5 10 15

Leu

<210> SEQ ID NO 5
<211> LENGTH: 16
<212> TYPE: PRT
<213> ORGANISM: Dengue virus 4

<400> SEQUENCE: 5

Gly Phe Gly Met Phe Thr Thr Asn Ile Trp Met Lys Phe Arg Glu Gly
1 5 10 15

<210> SEQ ID NO 6
<211> LENGTH: 16
<212> TYPE: PRT
<213> ORGANISM: Dengue virus 4

<400> SEQUENCE: 6

Cys Arg Ser Cys Thr Met Pro Pro Leu Arg Phe Leu Gly Glu Asp Gly
1 5 10 15

<210> SEQ ID NO 7
<211> LENGTH: 17
<212> TYPE: PRT
<213> ORGANISM: Dengue virus 4

<400> SEQUENCE: 7

Met Pro Pro Leu Arg Phe Leu Gly Glu Asp Gly Cys Trp Tyr Gly Met

Glu

<210> SEQ ID NO 8
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
atgaaatgca gctgggttat cttcttcctg atggcagtgg ttacaggggt caattcagag      60
gttcagctgc atcagtctgg ggcagagctt gtgaagccag ggcctcagt caagttgtcc      120 tgcacagttt ctggcttcaa cattaaagac acctatattc actgggtgaa acagaggcct     180
gaacagggcc tggagtggat tggaaggatt gatcctgcaa atggtaatac tgaatatgac     240
ccgaagttcc agggcaaggc cactataaaa gccgacactt cctccaacac agcctacctg     300
caactcatca gtctgacatc tgaggacact gccgtctatt actgtgcttt ttattactac     360
ggtcgtagcc ttgcttactg gggccaaggg actctggtca ctgtctctgc a              411
```

<210> SEQ ID NO 9
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Lys Cys Ser Trp Val Ile Phe Phe Leu Met Ala Val Val Thr Gly
1               5                   10                  15

Val Asn Ser Glu Val Gln Leu His Gln Ser Gly Ala Glu Leu Val Lys
            20                  25                  30

Pro Gly Ala Ser Val Lys Leu Ser Cys Thr Val Ser Gly Phe Asn Ile
        35                  40                  45

Lys Asp Thr Tyr Ile His Trp Val Lys Gln Arg Pro Glu Gln Gly Leu
    50                  55                  60

Glu Trp Ile Gly Arg Ile Asp Pro Ala Asn Gly Asn Thr Glu Tyr Asp
65                  70                  75                  80

Pro Lys Phe Gln Gly Lys Ala Thr Ile Lys Ala Asp Thr Ser Ser Asn
                85                  90                  95

Thr Ala Tyr Leu Gln Leu Ile Ser Leu Thr Ser Glu Asp Thr Ala Val
            100                 105                 110

Tyr Tyr Cys Ala Phe Tyr Tyr Tyr Gly Arg Ser Leu Ala Tyr Trp Gly
        115                 120                 125

Gln Gly Thr Leu Val Thr Val Ser Ala
    130                 135

<210> SEQ ID NO 10
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
atgagtgtgc ccactcaggt cctggggttg ctgctgctgt ggcttacaga tgccagatgt      60
```

```
gacatccaga tgactcagtc tccagcctcc ctatctgtgt ctgtgggaga aactgtcacc    120
atcacatgtc gaacaagtga gaatatttac agtagtttag catggtatca gcagaaacag    180
ggaaaatctc ctcagctcct ggtctatgct gcagctaact tagcggatgg tgtgccatca    240
aggttcagtg gcagtggatc aggcacacag tattccctca agatcaacag cctgcagtct    300
gaagattttg gaacttatta ctgtcaacat ttttgggta ctccgtggac gttcggtgga    360
ggcaccaagc tggaaatcaa a                                              381
```

<210> SEQ ID NO 11
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ala Ser Leu Ser
            20                  25                  30

Val Ser Val Gly Glu Thr Val Thr Ile Thr Cys Arg Thr Ser Glu Asn
        35                  40                  45

Ile Tyr Ser Ser Leu Ala Trp Tyr Gln Gln Lys Gln Gly Lys Ser Pro
    50                  55                  60

Gln Leu Leu Val Tyr Ala Ala Ala Asn Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Phe Gly Thr Tyr Tyr Cys Gln His Phe Trp
            100                 105                 110

Gly Thr Pro Trp Thr Phe Gly Gly Gly Thr Lys Leu Glu Ile Lys
        115                 120                 125
```

<210> SEQ ID NO 12
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
atgaaatgca gctgggtcat cttcttcctg atggcagtgg ttacaggggt caattcagag    60
gttcagctgc agcagtctgg ggctgagctt gtgaggccag ggccttagt caagttgtcc    120 tgcagagctt ctggcttcag aattagagac tactatatac actgggtgaa gcagaggcct    180
gaacagggcc tggagtggat tgatggatt gatcctgagt atggtaatac tatttatgac    240
ccgaacttcc ggggcaaggc cagtataaca tcagacacat cctccaacac agcctacctg    300
cagctcagca gcctgtcttc tgaggacaca gccgtctatt actgtgcctc gtattattac    360
ggtggtgtga actactgggg ccaaggcacc actctcacag tctcctca                408
```

<210> SEQ ID NO 13
<211> LENGTH: 136
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 13

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Leu Val Lys Leu Ser Cys Arg Ala Ser Gly Phe Arg Ile
        35                  40                  45

Arg Asp Tyr Tyr Ile His Trp Val Lys Gln Arg Pro Glu Gln Gly Leu
    50                  55                  60

Glu Trp Ile Gly Trp Ile Asp Pro Glu Tyr Gly Asn Thr Ile Tyr Asp
65                  70                  75                  80

Pro Asn Phe Arg Gly Lys Ala Ser Ile Thr Ser Asp Thr Ser Ser Asn
                85                  90                  95

Thr Ala Tyr Leu Gln Leu Ser Ser Leu Ser Ser Glu Asp Thr Ala Val
            100                 105                 110

Tyr Tyr Cys Ala Ser Tyr Tyr Gly Gly Val Asn Tyr Trp Gly Gln
        115                 120                 125

Gly Thr Thr Leu Thr Val Ser Ser
    130                 135

<210> SEQ ID NO 14
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14 atggatttc aagtgcagat tttcagcttc ctgctaatca gtgcctcagt catactgtcc      60
agaggacaaa ttgttctcac ccagtctcca gcaatcatgt ctgcatctcc aggggagaag    120
gtcaccatga cctgcagtgc cagttcaagt gtaagtcgca tttactggta ccaggagaag    180
ccaggatcct cccccagact cctgatttat gacacatcca acctggcttc tggagtccct    240
gttcgcttca gtggcagtgg gtctgggacc tcttactctc tcacaatcag ccgaatggag    300
gctgaagatg ctgccactta ttactgccag cagtggagta gttacccacg acgttcggt     360 ggaggcacca agctggaaat caaa                                           384

<210> SEQ ID NO 15
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Asp Phe Gln Val Gln Ile Phe Ser Phe Leu Leu Ile Ser Ala Ser
1               5                   10                  15

Val Ile Leu Ser Arg Gly Gln Ile Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Val Ser Arg Ile Tyr Trp Tyr Gln Glu Lys Pro Gly Ser Ser
    50                  55                  60

Pro Arg Leu Leu Ile Tyr Asp Thr Ser Asn Leu Ala Ser Gly Val Pro
65                  70                  75                  80

Val Arg Phe Ser Gly Ser Gly Ser Gly Thr Ser Tyr Ser Leu Thr Ile
            85                  90                  95

Ser Arg Met Glu Ala Glu Asp Ala Ala Thr Tyr Tyr Cys Gln Gln Trp
        100                 105                 110

Ser Ser Tyr Pro Arg Thr Phe Gly Gly Gly Thr Lys Leu Glu Ile Lys
    115                 120                 125

<210> SEQ ID NO 16
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atggaatgta actggatact ccttttatt ctgtcagtaa cttcaggtgt ctactcacag      60
gtgcagctcc agcagtctgg gactgagctg gcaagacctg gggcttcagt gaaattgtcc    120
tgtaaggctt ctggctacac ctttactaat tactggatac agtgggtaaa acagaggcct    180
ggacagggtc tggaatggat tgggatatt tatcctggag atggtgatac taggtacact    240
cagaagttca gggcaaggc catattgact gcagataaat cctccagcac agcctatatg    300
gaactcagca gtttggcatc tgaggactct gcggtctatt actgtgcctc actaacctgg    360
ggccaaggca ccactctcac agtctccaca                                     390

<210> SEQ ID NO 17
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Glu Cys Asn Trp Ile Leu Pro Phe Ile Leu Ser Val Thr Ser Gly
1               5                   10                  15

Val Tyr Ser Gln Val Gln Leu Gln Gln Ser Gly Thr Glu Leu Ala Arg
            20                  25                  30

Pro Gly Ala Ser Val Lys Leu Ser Cys Lys Ala Ser Gly Tyr Thr Phe
        35                  40                  45

Thr Asn Tyr Trp Ile Gln Trp Val Lys Gln Arg Pro Gly Gln Gly Leu
    50                  55                  60

Glu Trp Ile Gly Asp Ile Tyr Pro Gly Asp Gly Asp Thr Arg Tyr Thr
65                  70                  75                  80

Gln Lys Phe Arg Gly Lys Ala Ile Leu Thr Ala Asp Lys Ser Ser Ser
            85                  90                  95

Thr Ala Tyr Met Glu Leu Ser Ser Leu Ala Ser Glu Asp Ser Ala Val
        100                 105                 110

Tyr Tyr Cys Ala Ser Leu Thr Trp Gly Gln Gly Thr Thr Leu Thr Val
    115                 120                 125

Ser Thr
    130

<210> SEQ ID NO 18
<211> LENGTH: 399

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
atggaatcac agactcaggt cctcatgtcc ctgctgttct gggtatctgg tacctgtggg      60
gacattgtga tgacacagtc tccatcctcc ctgactgtga cagcaggaga gaaggtcact     120
atgagctgca ggtccagtca gagtctgtta aacagtggaa atcaaaagaa ctacttgacc     180
tggtaccagc agagaccagg gcagcctcct aaactgctga tctactgggc atccactagg     240
gaatctgggg tccctgatcg cttcacaggc agtggatctg gaacagattt cattctcacc     300
atcagcagtg tgcaggctga agacctggca gtttattact gtcagaatga gtatagttat     360
ccgctcacgt tcggtgctgg gaccaagctg gagctgaaa                            399
```

<210> SEQ ID NO 19
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
            20                  25                  30

Val Thr Ala Gly Glu Lys Val Thr Met Ser Cys Arg Ser Ser Gln Ser
        35                  40                  45

Leu Leu Asn Ser Gly Asn Gln Lys Asn Tyr Leu Thr Trp Tyr Gln Gln
    50                  55                  60

Arg Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Ile Leu Thr Ile Ser Ser Val Gln Ala Glu Asp Leu Ala Val Tyr
            100                 105                 110

Tyr Cys Gln Asn Glu Tyr Ser Tyr Pro Leu Thr Phe Gly Ala Gly Thr
        115                 120                 125

Lys Leu Glu Leu Lys
    130
```

<210> SEQ ID NO 20
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
atgaaatgca gctgggtcat cttcttcctg atggcagtgg ttacaggggt caactcagag      60
gttcagctgc agcagtctgg ggctgagttt atgaggccag ggccttagt caagttgtcc     120 tgcaaagctt ctggcttcaa cattaaagac tactatatgc attgggtgaa acagaggcct     180
gaacagggcc tggagtggat tggatggatt gaccctgaga atggtaatac tatatatgac     240
```

```
ccgaagttcc agggcaaggc cagtataaca gcagacacat cctccaacac agcctacctg    300
cagctcagca gcctgacttc tgaggacact gccgtctatt actgtgcctc gtattactac    360
ggtggtgtga actactgggg ccaaggcacc actctcacag tctcctca                 408
```

<210> SEQ ID NO 21
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Phe Met Arg
            20                  25                  30

Pro Gly Ala Leu Val Lys Leu Ser Cys Lys Ala Ser Gly Phe Asn Ile
        35                  40                  45

Lys Asp Tyr Tyr Met His Trp Val Lys Gln Arg Pro Glu Gln Gly Leu
    50                  55                  60

Glu Trp Ile Gly Trp Ile Asp Pro Glu Asn Gly Asn Thr Ile Tyr Asp
65                  70                  75                  80

Pro Lys Phe Gln Gly Lys Ala Ser Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Ser Tyr Tyr Tyr Gly Gly Val Asn Tyr Trp Gly Gln
        115                 120                 125

Gly Thr Thr Leu Thr Val Ser Ser
    130                 135
```

<210> SEQ ID NO 22
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
atggatttc aagtgcagat tttcagcttc ctgctaatca gtgcctcagt cattctgtcc    60
agaggacaaa ttgttctcac ccagtctcca gcaatcatgt ctgcatctcc aggggagaag   120
gtcaccatga cctgcagtgc cagctcaact gtaagttcca tttactggtt ccagcagagg   180
ccaggatcct cccccagact cctgatttat gacacatcgt aactggcttc tggagtccct   240
attcgcttca ctggcagtgg gtctgggacc tcttactctc tcacaatcag ccgaatgggg   300
gctgaagatg ctgccactta ttactgccag cagtggagta gttacccacg acgttcggt    360 ggaggcacca agctggaaat caaa                                          384
```

<210> SEQ ID NO 23
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Met Asp Phe Gln Val Gln Ile Phe Ser Phe Leu Leu Ile Ser Ala Ser
1               5                   10                  15

Val Ile Leu Ser Arg Gly Gln Ile Val Leu Thr Gln Ser Pro Ala Ile
                20                  25                  30

Met Ser Ala Ser Pro Gly Glu Lys Val Thr Met Thr Cys Ser Ala Ser
            35                  40                  45

Ser Thr Val Ser Ser Ile Tyr Trp Phe Gln Gln Arg Pro Gly Ser Ser
    50                  55                  60

Pro Arg Leu Leu Ile Tyr Asp Thr Ser Lys Leu Ala Ser Gly Val Pro
65                  70                  75                  80

Ile Arg Phe Thr Gly Ser Gly Ser Gly Thr Ser Tyr Ser Leu Thr Ile
                85                  90                  95

Ser Arg Met Gly Ala Glu Asp Ala Ala Thr Tyr Tyr Cys Gln Gln Trp
            100                 105                 110

Ser Ser Tyr Pro Arg Thr Phe Gly Gly Gly Thr Lys Leu Glu Ile Lys
    115                 120                 125
```

<210> SEQ ID NO 24
<211> LENGTH: 414
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
atggctgtcc tggtgctgtt cctctgcctg gttgcatttc caagctgtgt cctgtcccag      60
gtgcagctga aggagtcagg acctggcctg gtggcgccct cacagagcct gtccatcact     120
tgcactgtct ctgggttttc attaaccagc tatggtgtac actgggttcg ccagcctcca     180
ggaaagggtc tggagtggct gggagtaata tggcctggtg gaagcacaaa ttataattcg     240
gctctcatgt ccagactgag catcagcaaa gacagttcca agagccaagt tttcttaaaa     300
atgaacagtc tgcaacctga tgacacagcc atatactact gtgccagaga gccgatctac     360
ggtagtaggt acttcgatgt ctggggcgca gggaccacgg tcaccgtctc ctca           414
```

<210> SEQ ID NO 25
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Met Ala Val Leu Val Leu Phe Leu Cys Leu Val Ala Phe Pro Ser Cys
1               5                   10                  15

Val Leu Ser Gln Val Gln Leu Lys Glu Ser Gly Pro Gly Leu Val Ala
                20                  25                  30

Pro Ser Gln Ser Leu Ser Ile Thr Cys Thr Val Ser Gly Phe Ser Leu
            35                  40                  45

Thr Ser Tyr Gly Val His Trp Val Arg Gln Pro Pro Gly Lys Gly Leu
    50                  55                  60

Glu Trp Leu Gly Val Ile Trp Pro Gly Gly Ser Thr Asn Tyr Asn Ser
65                  70                  75                  80

Ala Leu Met Ser Arg Leu Ser Ile Ser Lys Asp Ser Ser Lys Ser Gln
                85                  90                  95
```

```
Val Phe Leu Lys Met Asn Ser Leu Gln Pro Asp Asp Thr Ala Ile Tyr
            100                 105                 110

Tyr Cys Ala Arg Glu Pro Ile Tyr Gly Ser Arg Tyr Phe Asp Val Trp
        115                 120                 125

Gly Ala Gly Thr Thr Val Thr Val Ser Ser
    130                 135

<210> SEQ ID NO 26
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
atggtatcca cacctcagtt ccttgtattt tgcttttct ggattccagc ctccagaggt      60
gacatcctgc tgactcagtc tccagccatc ctgtctgtga gtccaggaga aagagtcact     120
ctctcctgca gggccagtca gagcattggc acaagaatac actggtatca gcaagaaaca    180
aatggttctc caaggcttct cataaagttt gcttttgagt ctatctctgg atccctttcc    240
aggtttagtg gcagtggatc aggacagat tttactctta gcatcaacag tgtggagtct     300
gaagatattg cagagtatta ctgtcaacag agtattaact ggccgctcac gttcggtgct    360
gggaccaagc tggaactgaa a                                              381

<210> SEQ ID NO 27
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Val Ser Thr Pro Gln Phe Leu Val Phe Leu Phe Trp Ile Pro
1               5                   10                  15

Ala Ser Arg Gly Asp Ile Leu Leu Thr Gln Ser Pro Ala Ile Leu Ser
            20                  25                  30

Val Ser Pro Gly Glu Arg Val Thr Leu Ser Cys Arg Ala Ser Gln Ser
        35                  40                  45

Ile Gly Thr Arg Ile His Trp Tyr Gln Gln Arg Thr Asn Gly Ser Pro
    50                  55                  60

Arg Leu Leu Ile Lys Phe Ala Phe Glu Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Ser Glu Asp Ile Ala Glu Tyr Tyr Cys Gln Gln Ser Ile
            100                 105                 110

Asn Trp Pro Leu Thr Phe Gly Ala Gly Thr Lys Leu Glu Leu Lys
        115                 120                 125

<210> SEQ ID NO 28
<211> LENGTH: 16
<212> TYPE: PRT
<213> ORGANISM: Dengue virus 2

<400> SEQUENCE: 28

Thr Glu Leu Lys Tyr Ser Trp Lys Thr Trp Gly Lys Ala Lys Met Leu
1               5                   10                  15
```

<210> SEQ ID NO 29
<211> LENGTH: 353
<212> TYPE: PRT
<213> ORGANISM: Dengue virus 1

<400> SEQUENCE: 29

```
Asp Ser Gly Cys Val Ile Asn Trp Lys Gly Arg Glu Leu Lys Cys Gly
1               5                   10                  15

Ser Gly Ile Phe Val Thr Asn Glu Val His Thr Trp Thr Glu Gln Tyr
            20                  25                  30

Lys Phe Gln Ala Asp Ser Pro Lys Arg Leu Ser Ala Ala Ile Gly Lys
        35                  40                  45

Ala Trp Glu Glu Gly Val Cys Gly Ile Arg Ser Ala Thr Arg Leu Glu
    50                  55                  60

Asn Ile Met Trp Lys Gln Ile Ser Asn Glu Leu Asn His Ile Leu Leu
65                  70                  75                  80

Glu Asn Asp Met Lys Phe Thr Val Val Gly Asp Val Val Gly Ile
                85                  90                  95

Leu Ala Gln Gly Lys Lys Met Ile Arg Pro Gln Pro Met Glu His Lys
            100                 105                 110

Tyr Ser Trp Lys Ser Trp Gly Lys Ala Lys Ile Ile Gly Ala Asp Ile
        115                 120                 125

Gln Asn Thr Thr Phe Ile Ile Asp Gly Pro Asp Thr Pro Glu Cys Pro
    130                 135                 140

Asp Asp Gln Arg Ala Trp Asn Ile Trp Glu Val Glu Asp Tyr Gly Phe
145                 150                 155                 160

Gly Ile Phe Thr Thr Asn Ile Trp Leu Lys Leu Arg Asp Ser Tyr Thr
                165                 170                 175

Gln Met Cys Asp His Arg Leu Met Ser Ala Ala Ile Lys Asp Ser Lys
            180                 185                 190

Ala Val His Ala Asp Met Gly Tyr Trp Ile Glu Ser Glu Lys Asn Glu
        195                 200                 205

Thr Trp Lys Leu Ala Arg Ala Ser Phe Ile Glu Val Lys Thr Cys Val
    210                 215                 220

Trp Pro Lys Ser His Thr Leu Trp Ser Asn Gly Val Leu Glu Ser Glu
225                 230                 235                 240

Met Ile Ile Pro Lys Ile Tyr Gly Gly Pro Ile Ser Gln His Asn Tyr
                245                 250                 255

Arg Pro Gly Tyr Phe Thr Gln Thr Ala Gly Pro Trp His Leu Gly Lys
            260                 265                 270

Leu Glu Leu Asp Phe Asp Leu Cys Glu Gly Thr Thr Val Val Val Asp
        275                 280                 285

Glu His Cys Gly Asn Arg Gly Pro Ser Leu Arg Thr Thr Thr Val Thr
    290                 295                 300

Gly Lys Ile Ile His Glu Trp Cys Cys Arg Ser Cys Thr Leu Pro Pro
305                 310                 315                 320

Leu Arg Phe Lys Gly Glu Asp Gly Cys Trp Tyr Gly Met Glu Ile Arg
                325                 330                 335

Pro Val Lys Glu Lys Glu Glu Asn Leu Val Lys Ser Met Val Ser Ala
            340                 345                 350

Gly
```

<210> SEQ ID NO 30

<211> LENGTH: 357
<212> TYPE: PRT
<213> ORGANISM: Dengue virus 2

<400> SEQUENCE: 30

```
Val Met Val Gln Ala Asp Ser Gly Cys Val Ser Trp Lys Asn Lys
1               5                   10                  15
Glu Leu Lys Cys Gly Ser Gly Ile Phe Ile Thr Asp Asn Val His Thr
            20                  25                  30
Trp Thr Glu Gln Tyr Lys Phe Gln Pro Glu Ser Pro Ser Lys Leu Ala
        35                  40                  45
Ser Ala Ile Gln Lys Ala His Glu Glu Gly Ile Cys Gly Ile Arg Ser
    50                  55                  60
Val Thr Arg Leu Glu Asn Leu Met Trp Lys Gln Ile Thr Pro Glu Leu
65                  70                  75                  80
Asn His Ile Leu Ser Glu Asn Glu Val Lys Leu Thr Ile Met Thr Gly
                85                  90                  95
Asp Ile Lys Gly Ile Met Gln Ala Gly Lys Arg Ser Leu Gln Pro Gln
            100                 105                 110
Pro Thr Glu Leu Lys Tyr Ser Trp Lys Thr Trp Gly Lys Ala Lys Met
        115                 120                 125
Leu Ser Thr Glu Ser His Asn Gln Thr Phe Leu Ile Asp Gly Pro Glu
    130                 135                 140
Thr Ala Glu Cys Pro Asn Thr Asn Arg Ala Trp Asn Ser Leu Glu Val
145                 150                 155                 160
Glu Asp Tyr Gly Phe Gly Val Phe Thr Thr Asn Ile Trp Leu Lys Leu
                165                 170                 175
Arg Glu Lys Gln Asp Val Phe Cys Asp Ser Lys Leu Met Ser Ala Ala
            180                 185                 190
Ile Lys Asp Asn Arg Ala Val His Ala Asp Met Gly Tyr Trp Ile Glu
        195                 200                 205
Ser Ala Leu Asn Asp Thr Trp Lys Ile Glu Lys Ala Ser Phe Ile Glu
    210                 215                 220
Val Lys Ser Cys His Trp Pro Lys Ser His Thr Leu Trp Ser Asn Gly
225                 230                 235                 240
Val Leu Glu Ser Glu Met Ile Ile Pro Lys Asn Phe Ala Gly Pro Val
                245                 250                 255
Ser Gln His Asn Tyr Arg Pro Gly Tyr His Thr Gln Thr Ala Gly Pro
            260                 265                 270
Trp His Leu Gly Lys Leu Glu Met Asp Phe Asp Phe Cys Glu Gly Thr
        275                 280                 285
Thr Val Val Val Thr Glu Asp Cys Gly Asn Arg Gly Pro Ser Leu Arg
    290                 295                 300
Thr Thr Thr Ala Ser Gly Lys Leu Ile Thr Glu Trp Cys Cys Arg Ser
305                 310                 315                 320
Cys Thr Leu Pro Pro Leu Arg Tyr Arg Gly Asp Gly Cys Trp Tyr
                325                 330                 335
Gly Met Glu Ile Arg Pro Leu Lys Glu Lys Glu Glu Asn Leu Val Asn
            340                 345                 350
Ser Leu Val Thr Ala
        355
```

<210> SEQ ID NO 31
<211> LENGTH: 353
<212> TYPE: PRT

<213> ORGANISM: Dengue virus 3

<400> SEQUENCE: 31

Asp Met Gly Cys Val Ile Asn Trp Lys Gly L

Asp Met Gly Cys Val Ser Trp Ser Gly Lys Glu Leu Lys Cys Gly
1               5                   10                  15

Ser Gly Ile Phe Val Ala Asp Asn Val His Thr Trp Thr Glu Gln Tyr
            20                  25                  30

Lys Phe Gln Pro Glu Ser Pro Ala Arg Leu Ala Ser Ala Ile Leu Asn
        35                  40                  45

Ala His Lys Asp Gly Val Cys Gly Ile Arg Ser Thr Thr Arg Leu Glu
    50                  55                  60

Asn Val Met Trp Lys Gln Ile Thr Asn Glu Leu Asn Tyr Val Leu Trp
65                  70                  75                  80

Glu Gly Gly His Asp Leu Thr Val Val Ala Gly Asp Val Lys Gly Val
                85                  90                  95

Leu Thr Lys Gly Lys Arg Ala Leu Thr Pro Val Asn Asp Leu Lys
            100                 105                 110

Tyr Ser Trp Lys Thr Trp Gly Lys Ala Lys Ile Phe Thr Pro Glu Ala
            115                 120                 125

Arg Asn Ser Thr Phe Leu Ile Asp Gly Pro Asp Thr Ser Glu Cys Pro
        130                 135                 140

Asn Glu Arg Arg Ala Trp Asn Phe Leu Glu Val Glu Asp Tyr Gly Phe
145                 150                 155                 160

Gly Met Phe Thr Thr Asn Ile Trp Met Lys Phe Arg Glu Gly Ser Ser
                165                 170                 175

Glu Val Cys Asp His Arg Leu Met Ser Ala Ala Ile Lys Asp Gln Lys
            180                 185                 190

Ala Val His Ala Asp Met Gly Tyr Trp Ile Glu Ser Lys Asn Gln
        195                 200                 205

Thr Trp Gln Ile Glu Lys Ala Ser Leu Ile Glu Val Lys Thr Cys Leu
    210                 215                 220

Trp Pro Lys Thr His Thr Leu Trp Ser Asn Gly Val Leu Glu Ser Gln
225                 230                 235                 240

Met Leu Ile Pro Lys Ser Tyr Ala Gly Pro Phe Ser Gln His Asn Tyr
                245                 250                 255

Arg Gln Gly Tyr Ala Thr Gln Thr Val Gly Pro Trp His Leu Gly Lys
            260                 265                 270

Leu Glu Ile Asp Phe Gly Glu Cys Pro Gly Thr Thr Val Thr Ile Gln
        275                 280                 285

Glu Asp Cys Asp His Arg Gly Pro Ser Leu Arg Thr Thr Thr Ala Ser
    290                 295                 300

Gly Lys Leu Val Thr Gln Trp Cys Cys Arg Ser Cys Thr Met Pro Pro
305                 310                 315                 320

Leu Arg Phe Leu Gly Glu Asp Gly Cys Trp Tyr Gly Met Glu Ile Arg
                325                 330                 335

Pro Leu Ser Glu Lys Glu Glu Asn Met Val Lys Ser Gln Val Thr Ala
            340                 345                 350

Gly

<210> SEQ ID NO 33
<211> LENGTH: 11
<212> TYPE: PRT
<213> ORGANISM: Dengue virus 1

<400> SEQUENCE: 33

Tyr Gly Gly Pro Ile Ser Gln His Asn Tyr Arg
1               5                   10

-continued

```
<210> SEQ ID NO 34
<211> LENGTH: 15
<212> TYPE: PRT
<213> ORGANISM: Dengue virus 1

<400> SEQUENCE: 34

Met Ile Arg Pro Gln Pro Met Glu His Lys Tyr Ser Trp Lys Ser
1               5                   10                  15

<210> SEQ ID NO 35
<211> LENGTH: 15
<212> TYPE: PRT
<213> ORGANISM: Dengue virus 1

<400> SEQUENCE: 35

His Lys Tyr Ser Trp Lys Ser Trp Gly Lys Ala Lys Ile Ile Gly
1               5                   10                  15

<210> SEQ ID NO 36
<211> LENGTH: 10
<212> TYPE: PRT
<213> ORGANISM: Dengue virus 2

<400> SEQUENCE: 36

Gly Gly Pro Val Ser Gln His Asn Tyr Arg
1               5                   10

<210> SEQ ID NO 37
<211> LENGTH: 15
<212> TYPE: PRT
<213> ORGANISM: Dengue virus 1

<400> SEQUENCE: 37

Ile Trp Leu Lys Leu Arg Asp Ser Tyr Thr Gln Met Cys Asp His
1               5                   10                  15
```

ANTI-DENGUE VIRUS NS1 PROTEIN MONOCLONAL ANTIBODIES

RELATED APPLICATIONS

This application is a divisional of U.S. application Ser. No. 15/429,756, filed on Feb. 10, 2017, which claims the benefit of U.S. Provisional Application No. 62/293,990, filed on Feb. 11, 2016. The entire teachings of the above applications are incorporated herein by reference.

GOVERNMENT SUPPORT

This invention was made with Government support under grant number R33 AI100190 awarded by National Institutes of Health. The government has certain rights in the invention.

BACKGROUND OF THE INVENTION

Dengue virus (DV) is a mosquito-borne pathogen that causes dengue fever (DF) and severe life threatening illness, dengue hemorrhagic fever/dengue shock syndrome (DHF/DSS). DV is a small, enveloped, positive-stranded RNA virus that belongs to the Flavivirus genus of the Flaviviridae family which also includes Zika virus, and yellow fever virus. Four distinct subtypes or serotypes of dengue viruses (DV-1 to DV-4) are transmitted to humans through the bites of mosquito species *Aedes aegypti* and *Aedes albopictus*. It has been estimated that 50-100 million cases of DF and 250,000-500000 cases of DHF occur every year. Dengue constitutes a significant international public health concern, as two-fifths of the world's population live in dengue endemic regions, and an estimated 50-100 million cases of dengue infection occur annually. Furthermore 2.5 billion people are at risk for infection in subtropical and tropical regions of the world in the absence of effective intervention.

There are four dengue virus subtypes: dengue-1 (DV1), dengue-2 (DV2), dengue-3 (DV3), and dengue-4 (DV4). Each one of these subtypes form an antigenically distinct subgroup within the Flavivirus family. Despite extensive cross-reactivity among these viruses in serological tests, there is no cross-protective immunity in humans. Individuals living in an endemic area can have as many as four infections, one with each serotype, during their lifetimes.

DV encodes a nonstructural glycoprotein, NS1 (FIG. 16), which associates with intracellular membranes and the cell surface. NS1 is eventually secreted as a soluble hexamer from DV-infected cells and circulates in the bloodstream of infected patients. Therefore, NS1 serves as a convenient target antigen for detecting and diagnosing infection of a human patient potentially infected with one or more serotypes of dengue virus by providing a blood sample from such patient for testing.

While it is desirable to be able to detect all four dengue serotypes, implementation of a single assay that is highly sensitive for all serotypes has been hampered by limited relatedness of the viral targets at the nucleic acid level. Therefore, there remains a need to develop an accurate diagnostic that can detect and distinguish between all four dengue virus serotypes.

SUMMARY OF THE INVENTION

The present invention provides novel monoclonal antibodies and matched antibody pairs of the monoclonal antibodies of the invention for the specific detection of one or more of the four dengue virus serotypes in a biological sample that may contain one or more of such dengue virus serotypes. The antibodies of the invention facilitate the development of confirmatory in vitro diagnostic tests that detect and distinguish the presence of one or more dengue virus serotypes in a biological sample, preferably a sample derived from human subject. The invention further provides matched monoclonal antibody pairs wherein one or both members of the matched pair are bound to various particles or solid phases, with or without conjugated labels of any type. The invention also provides kits containing the matched antibody pairs of the invention. The invention also provides monoclonal antibodies specific for one or more of DV1, DV2, DV3 or DV4 that are useful as therapeutics for the prevention and treatment of dengue virus infection and disorders relating to dengue virus infection.

Combinations of these antibodies also allows a Pan detection of any of the 4 serotypes of dengue on one strip. In addition to be able to detect serotypes in each individual strip or all the serotypes in one strips, other configurations would include each of the serotypes in particular areas of only one strip. The use of combinations of antibody pairs can be adapted to multiple strips or one strips with multiple detection areas.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 shows the signal patterns in detecting the four dengue virus serotype NS1 proteins using a lateral flow sandwich format. Each lane of each test for serotype specificity to D1, DV2, DV3 or DV4 includes a different antibody pair. The antibody pair represented in each lane of each respective test for serotype specificity is indicated as either the capture antibody located at the test line (paper) or the detection antibody which in this case is conjugated to a colorimetric nanoparticle (NP) and represented. The antibodies in the first 4 lanes of each serotype specificity test are: Lane 1=Ab 271 (paper) and Ab 912 (NP); Lane 2=Ab 1 (paper) and Ab 164 (NP); Lane 3=Ab55 (paper) and Ab 411 (NP); Lane 4=Ab 55 (paper) and Ab 626 (NP). The tests showing 5 lanes have the same antibody pairs in Lane 1-4. Lane 5 is a pan detection of dengue wherein the antibody on the paper is Ab 323 and the antibodies with the NP detection label are Abs 271, 164, 411 and 626.

FIG. 3 shows experimental data from lateral flow assays indicating that the 725-55/725-411 antibody pair is specific for detecting dengue NS1 serotype 3 protein. This pair is interchangeable (reversible) on the paper and on the nanoparticles. "Brazil" and "Asia" refer to viral strains from different geographic areas.

FIG. 10 shows the sequences of peptides that are recognized by the individual antibodies shown in FIG. 9 in an immunoblot assay.

FIG. 14 shows peptides recognized by antibody 626 in peptide screening assay.

FIG. 15 shows peptides recognized by antibody 271 in peptide screening assay.

FIG. 18 shows the DNA and Amino Acid sequences of the heavy and light chains of antibody 55. The order of each sequence is as follows: leader sequence-FR1-CDR1-FR2-CDK-FR3-CDR3-FR4. In the figure, the leader sequence is plain text. The first framework region (FR1) is underlined. The first CDR region (CDR1) is underlined with a wavy line. The second framework region (FR2) is underlined with a double underline. The second CDR region (CDR2) is underlined with a dotted and dashed line. The third framework region (FR3) is underlined with a solid thick underline. The third CDR region (CDR3) is underlined with large dashes. The fourth framework region (FR4) is underlined with small dots.

FIG. 19 shows the DNA and Amino Acid sequences of the heavy and light chains of antibody 271. The order of each sequence is as follows: leader sequence-FR1-CDR1-FR2-CDR2-FR3-CDR3-FR4 In the figure, the leader sequence is plain text. The first framework region (FR1) is underlined. The first CDR region (CDR1) is underlined with a wavy line. The second framework region (FR2) is underlined with a double underline. The second CDR region (CDR2) is underlined with a dotted and dashed line. The third framework region (FR3) is underlined with a solid thick underline. The third CDR region (CDR3) is underlined with large dashes. The fourth framework region (FR4) is underlined with small dots.

FIG. 20 shows the DNA and Amino Acid sequences of the heavy and light chains of antibody 323. The order of each sequence is as follows: leader sequence-FR1-CDR1-FR2-CDR2-FR3-CDR3-FR4 In the figure, the leader sequence is plain text. The first framework region (FR1) is underlined. The first CDR region (CDR1) is underlined with a wavy line. The second framework region (FR2) is underlined with a double underline. The second CDR region (CDR2) is underlined with a dotted and dashed line. The third framework region (FR3) is underlined with a solid thick underline. The third CDR region (CDR3) is underlined with large dashes. The fourth framework region (FR4) is underlined with small dots.

FIG. 21 shows the DNA and Amino Acid sequences of the heavy and light chains of antibody 411. The order of each sequence is as follows: leader sequence-FR1-CDR1-FR2-CDR2-FR3-CDR3-FR4 In the figure, the leader sequence is plain text. The first framework region (FR1) is underlined. The first CDR region (CDR1) is underlined with a wavy line. The second framework region (FR2) is underlined with a double underline. The second CDR region (CDR2) is underlined with a dotted and dashed line. The third framework region (FR3) is underlined with a solid thick underline. The third CDR region (CDR3) is underlined with large dashes. The fourth framework region (FR4) is underlined with small dots.

FIG. 22 shows the DNA and Amino Acid sequences of the heavy and light chains of antibody 626. The order of each sequence is as follows: leader sequence-FR1-CDR1-FR2-CDR2-FR3-CDR3-FR4 In the figure, the leader sequence is plain text. The first framework region (FR1) is underlined. The first CDR region (CDR1) is underlined with a wavy line. The second framework region (FR2) is underlined with a double underline. The second CDR region (CDR2) is underlined with a dotted and dashed line. The third framework region (FR3) is underlined with a solid thick underline. The third CDR region (CDR3) is underlined with large dashes. The fourth framework region (FR4) is underlined with small dots.

FIG. 27 is a sequence alignment of the four dengue serotype NS1 proteins showing the linear epitope mapping of the antibodies.

DETAILED DESCRIPTION OF THE INVENTION

Figure 2:
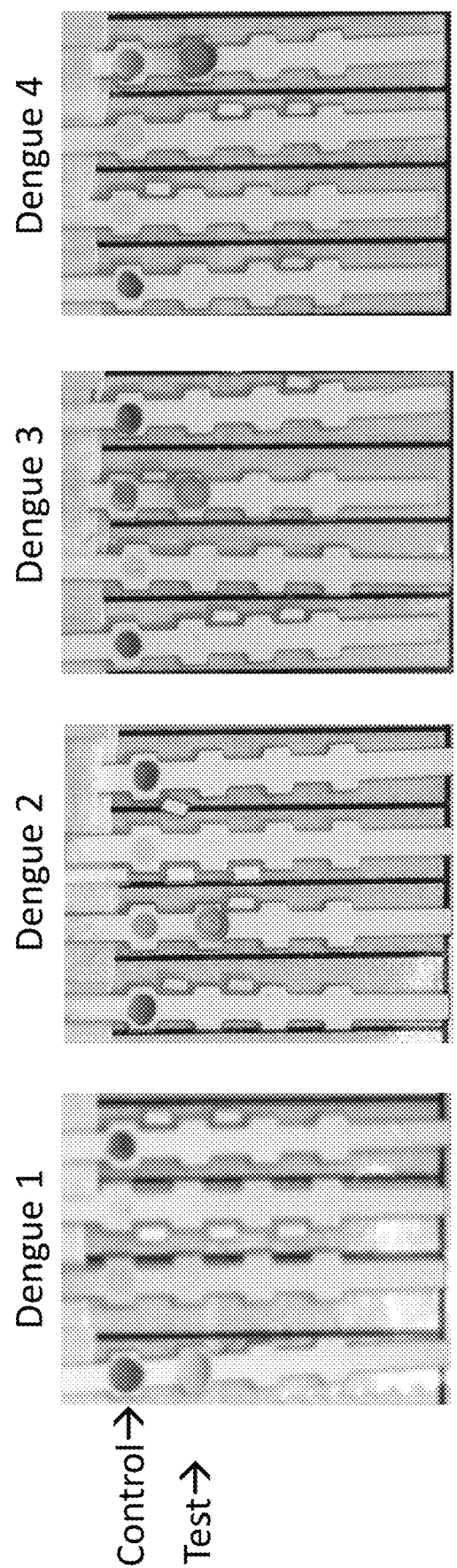
FIG. 2 shows experimental data used to define the pattern shown in Slide 1. The sample loaded onto the strips was supernatant from dengue-infected Vero cells. The order of the strips is as in FIG. 1.

The terms "a", "an" and "the" as used herein are defined to mean "one or more" and include the plural unless the context is inappropriate.

As is known in the art, an "antibody" is an immunoglobulin that binds specifically to a particular antigen. The term encompasses immunoglobulins that are naturally produced in that they are generated by an organism reacting to the antigen, and also those that are synthetically produced or engineered. An antibody may be monoclonal or polyclonal. An antibody may be a member of any immunoglobulin class, including any of the human classes: IgG, IgM, IgA, and IgD. A typical immunoglobulin (antibody) structural unit as understood in the art, is known to comprise a tetramer. Each tetramer is composed of two identical pairs of polypeptide chains, each pair having one "light" (approximately 25 kD) and one "heavy" chain (approximately 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains respectively. Each variable region is further subdivided into hypervariable (HV) and framework (FR) regions. The hypervariable regions comprise three areas of hypervariability sequence called complementarity determining regions (CDR 1, CDR 2 and CDR 3), separated by four framework regions (FR1, FR2, FR2, and FR4) which form a beta-sheet structure and serve as a scaffold to hold the HV regions in position. The C-terminus of each heavy and light chain defines a constant region consisting of one domain for the light chain (CL) and three for the heavy chain (CH1, CH2 and CH3). Preferably, the terms "full length" "whole" or "intact" are used in reference to an antibody to mean that it contains two heavy chains and two light chains, optionally associated by disulfide bonds as occurs with naturally-produced antibodies. Preferably, an antibody is produced by a cell. Preferably, an antibody is produced by chemical synthesis. Preferably, an antibody is derived from a mammal. Preferably, an antibody is derived from an animal such as, but not limited to, mouse, rat, horse, pig, or goat. Preferably, an antibody is produced using a recombinant cell culture system. Preferably, an antibody may be a purified antibody (for example, by immune-affinity chromatography). Preferably, an antibody may be a human antibody. Preferably, an antibody may be a humanized antibody (antibody from non-human species whose protein sequences have been modified to increase their similarity to antibody variants produced naturally in humans). Preferably, an antibody may be a chimeric antibody (antibody made by combining genetic material from a non-human source, e.g., mouse, rat, horse, or pig, with genetic material from humans).

"Antibody fragments" comprise a portion of an intact antibody, generally the antigen binding or variable region of the intact antibody. Examples of antibody fragments include Fab, Fab', F(ab')2, and Fv fragments: diabodies; single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. In addition to their specificity, the monoclonal antibodies can frequently be advantageous in that they are synthesized by the hybridoma culture, uncontaminated by other immunoglobulins. The "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Köhler et al., Nature, 256:495 (1975), or may be made by generally well known recombinant DNA methods. The "monoclonal antibodies" may also be isolated from phage antibody libraries using the techniques described in Clackson et al., Nature, 352:624-628 (1991) and Marks et al., J. Mol. Biol., 222:581-597 (1991), for example.

As used herein, the expressions "cell", "cell line," and "cell culture" are used interchangeably and all such designations include progeny. Thus, the words "transformants" and "transformed cells" include the primary subject cell and culture derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, this will be clear from the context.

The terms "polypeptide", "peptide", and "protein", as used herein, are interchangeable and are defined to mean a biomolecule composed of amino acids linked by a peptide bond.

The term "subtype" or "serotype" is used herein interchangeably and in reference to a virus, for example dengue virus, and means genetic variants of that virus antigen such that one subtype is recognized by an immune system apart from a different subtype. For example, dengue virus subtype 1 (DV1) is immunologically distinguishable from dengue virus subtype 2 (DV2).

As used in this invention, the term "epitope" means any antigenic determinant on an antigen to which the antibody binds.

The word "complex" as used herein refers to the product of a specific binding agent-ligand reaction. Preferably, the term "complex" as used herein refers to a labelled detection antibody bound to its target analyte prior to being detected by and bound to a capture antibody in a sandwich immunoassay.

The term "antigen" also referred to herein as "analyte" refers to a polypeptide or protein that is able to specifically bind to (immunoreact with) an antibody and form an immunoreaction product (immunocomplex). The site on the antigen with which the antibody binds is referred to as an antigenic determinant or epitope.

As used herein, the term "matched antibody pairs" refers to sets of antibodies which, when used together, are capable of specifically binding different epitopes on the same protein antigen, so they can be used together in a complex for the capture and detection of a single antigen for example, in a sandwich immunoassay. Specific binding for each antibody may be determined by measuring the binding affinity that an antibody has for an antigen using techniques well known to those of skill in the art. Preferably, matched antibody pairs of the invention specifically bind to only one serotype of the dengue NS1 protein, and not crossing reacting with other dengue virus serotypes or preferably, other NS1 proteins from related viruses such as zika virus or yellow fever virus that may be present in a biological sample being tested. Preferably, the matched antibody pairs are pairs of monoclonal antibodies.

As used herein a "sandwich immunoassay" is an assay using two antibodies, which bind to different sites on an antigen such as a specific serotype of the NS1 protein of the dengue virus. The capture antibody, which is highly specific for the antigen, is attached to a solid surface. Depending on the assay format, a second antibody referred to as the detection antibody comprising a detection label and that also binds the antigen at a different epitope than the capture antibody is contacted with a biological sample suspected of containing the target antigen and then subsequently contacted with the capture antibody. As a result, the antigen is 'sandwiched' between the two antibodies.

Figure 23:
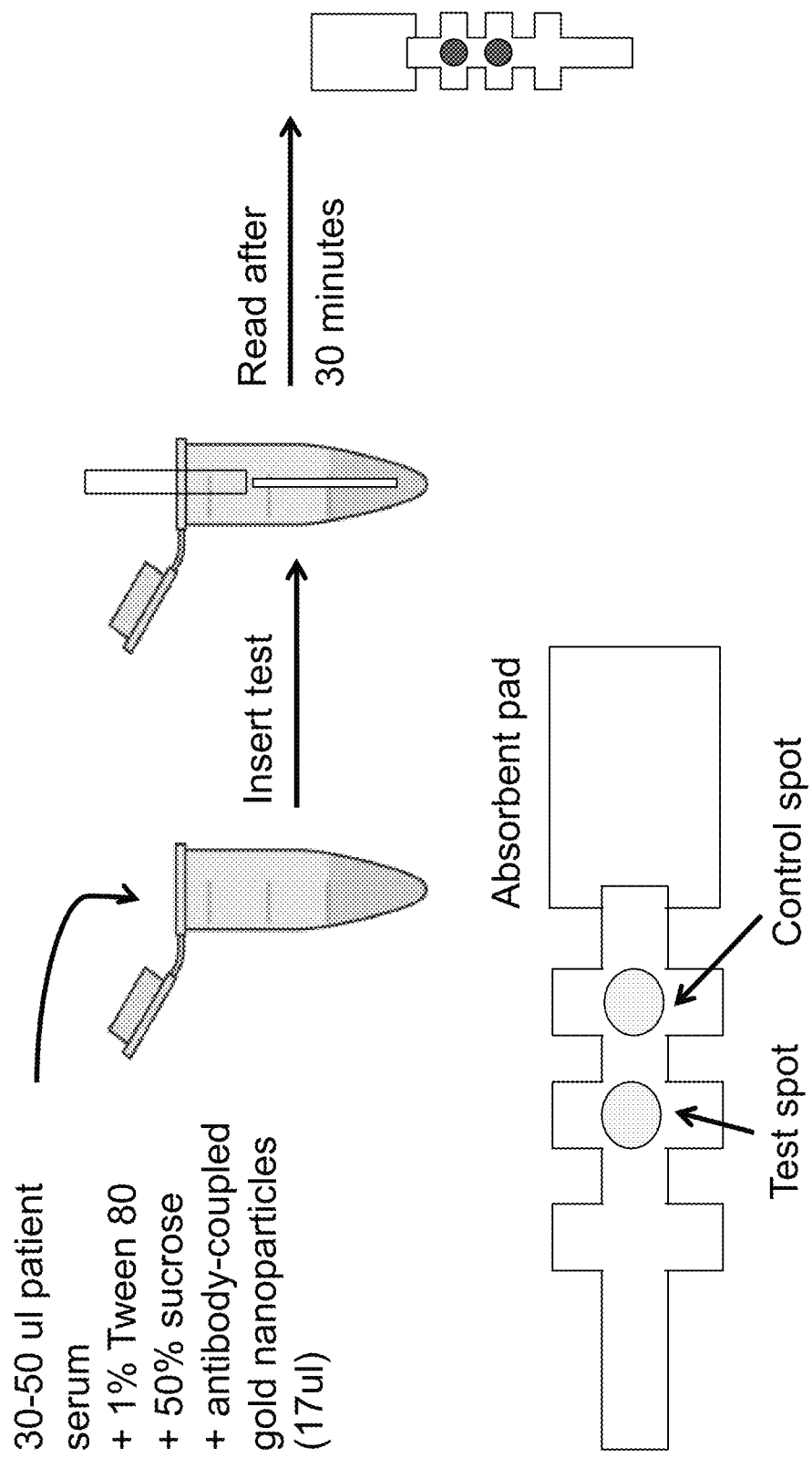
FIG. 23 illustrates one format of a lateral flow assay for use with the antibodies of the invention. This format is also referred to the "dipstick" or "half strip format".
Figure 24:
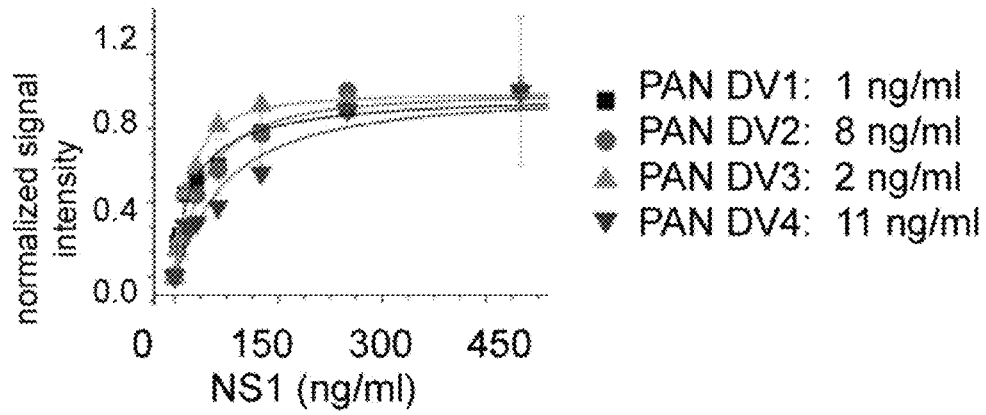
FIG. 24 illustrates the limits of detection for viral NS-1 proteins using a pan-dengue strip.
Figure 25:
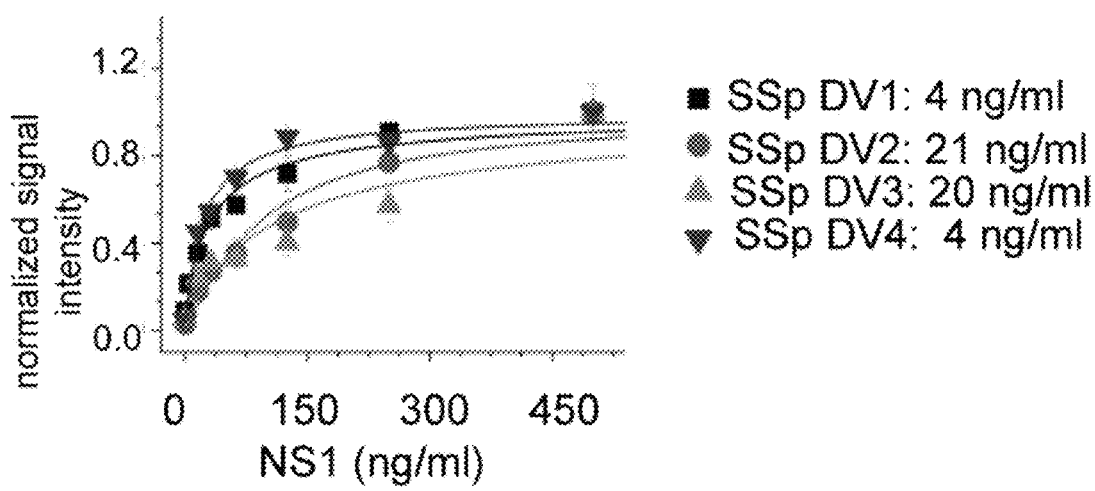
FIG. 25 illustrates the limits of detection for viral NS-1 proteins using serotype-specific (SSp) strips 1-4.
Figure 26:
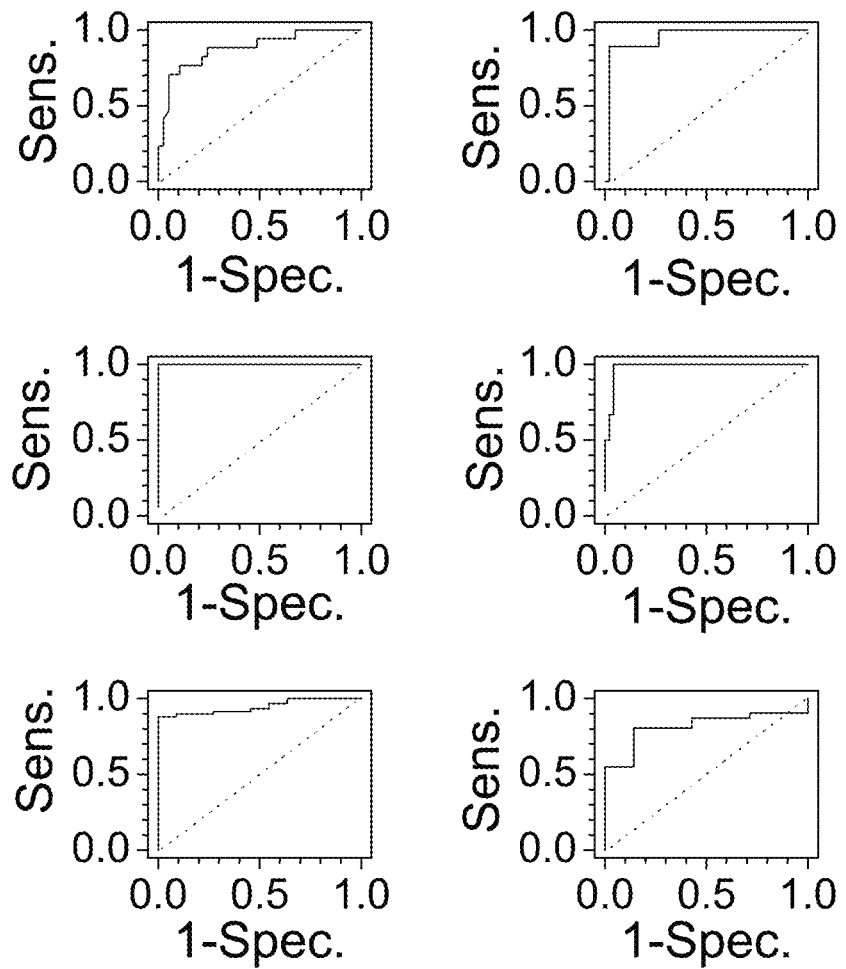
FIG. 26 provides ROC analysis and sensitivity/specificity analysis of the dengue virus.

"Lateral flow assays (LFA)" as that term is used herein are immunoassays that can be used to detect biological agents including various analytes in samples, including biological sample, that may contain such agents. The general format of LFA uses the same rationale as ELISA, where immobilized capture antibody or is bound onto a solid phase nitrocellulose membrane for example instead of a plastic well. The advantage of the LFA format is that the membrane enables a one-step assay unlike that found in the multiple-step ELISA. Based on the principal of high affinity, sensitivity and selectivity between specific antibody-antigen pairs, immunology-based assays are readily available due to the huge variety of existing antibodies and the potential to produce many more as well as the availability of reasonably priced reaction reagents. Lateral flow technology is well-suited to point-of-care (POC) disease diagnostics because it is robust and inexpensive, without requiring power, a cold chain for storage and transport, or specialized reagents. Many LFA devices comprise a matrix capable of supporting the test and which is made of a material which is capable of absorbing a liquid sample and which promotes capillary action of liquid sample along the matrix, such as nitrocellulose. The matrix may come in any shape or size, one common size being a strip that is capable of being held in a hand. In one exemplary test format, after absorbing the liquid sample onto the sample pad, the liquid moves into the conjugate pad by capillary action, rehydrates the conjugated particles labelled with a detectable moiety such as a colored label, allowing for the mixing of these particles with the absorbed liquid sample. The labelled conjugates interact with the specific analyte contained in the sample, thereby initiating the intermolecular interactions, which are dependent on the affinity and avidity of the reagents. Then the labelled conjugate and its specific analyte migrates towards the antibody at the test line thereby capturing and recognizing the labelled conjugate and its target analyte, where it becomes immobilized and produces a distinct signal for example, in the form of, for example, a colored line, indicating the test is positive. Excess reagents move past the capture lines to an optional control line comprising a positive control that insures that all reagents are functional and finally the excess reagents are entrapped in the wick pad, which is designed to draw the sample across the membrane by capillary action and thereby maintain a lateral flow along the chromatography strip. In another exemplary format sometimes referred to as "dipstick" or "half-strip" (FIG. 23), the labelled antibodies and serum are present in a container such as a test tube, wherein they become conjugated. A nitrocellulose membrane with a capture antibody bound to it on a test line is contacted with the labelled conjugate of antibody and target analyte in the container and migrates toward the test line where it is captured by the antibody at the test line wherein it become immobilized and produces a distinct signal, for example a colored line. Some lateral flow assays may have more than one test line for multiplex testing of multiple analytes. As used herein, the term "lateral flow" refers to capillary flow through a material in a horizontal direction, but will be understood to apply to the flow of a liquid from a point of application of the liquid to another lateral position even if, for example, the device is vertical or on an incline. Lateral flow depends upon properties of the liquid/substrate interaction (surface wetting or wicking action) and does not require or involve application of outside forces, e.g., vacuum or pressure applications by the user.

As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). Preferably, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM 120 weight residue table, a gap length penalty of 12 and a gap penalty of 4. The reference sequence can be, independently, a full length sequence (e.g., a $V_H$ or $V_L$ peptide) or a subsequence thereof, such as one or more CDRs or framework regions.

As used herein, the term "substantially" refers to the qualitative condition of exhibiting total or near-total extent or degree of a characteristic or property of interest.

The phrase "substantial identity" or "substantially identical" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., Basic local alignment search tool, *J. Mol. Biol.*, 215(3): 403-410, 1990; Altschul et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. Preferably, two sequences are considered to be substantially identical if at least 80%, 85%, 90%, 91%, 92%, 93%, 94%, 95%, 96%, 97%, 98%, 99% or more of their corresponding residues are identical over a relevant stretch of residues. Preferably, the relevant stretch is a complete sequence. Preferably, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues. The relevant stretch can be, independently, a full-length sequence (e.g., a VH or VL peptide) or a subsequence thereof, such as one or more CDRs or framework regions.

The term "biological sample," as used herein, refers to a sample of biological origin, or a sample derived from the sample of biological origin, preferably from human patient. The biological samples include, but are not limited to, blood, plasma, serum, saliva, cerebral spinal fluid, pleural fluid, milk, lymph, sputum, semen, urine, stool, tear, saliva, needle aspirate, external section of the skin, respiratory, intestinal, or genitourinary tract, tumor, organ, cell culture, cell culture constituent, tissue sample, tissue section, whole cell, cell constituent, cytospin, or cell smear. The term "biological sample" does not include samples containing target proteins that have been denatured or otherwise altered such that the protein is no longer in its native configuration.

The terms "patient" of "subject" as used herein refers to an animal. Preferably the animal is a mammal. More preferably the mammal is a human. A "patient" also refers to, for example, dogs, cats, horses, cows, pigs, guinea pigs, fish, birds and the like.

As used herein, the term "antiviral agent" refers to a class of medication used specifically for treating viral infections by inhibiting, deactivating, or destroying virus particles. In general, an antiviral agent may be or comprise a compound of any chemical class (e.g., a small molecule, metal, nucleic acid, polypeptide, lipid and/or carbohydrate). Preferably, an antiviral agent is or comprises an antibody or antibody mimic. Preferably an anti-viral agent is an an anti-dengue antibody of the invention (e.g. Ab 55, Ab 271, Ab323, Ab 411, Ab 626). Preferably, an antiviral agent is or comprises a nucleic acid agent (e.g., an antisense oligonucleotide, a siRNA, a shRNA, etc) or mimic thereof. Preferably, an antiviral agent is or comprises a small molecule. Preferably, an antiviral agent is or comprises a naturally-occurring compound (e.g., small molecule).

The term "combination therapy", as used herein, refers to those situations in which two or more different pharmaceutical agents are administered in overlapping regimens so that the subject is simultaneously exposed to both agents.

The term "comparable" is used herein to describe two (or more) sets of conditions or circumstances that are sufficiently similar to one another to permit comparison of results obtained or phenomena observed. Preferably, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

As used herein, the term "corresponding to" is often used to designate the position/identity of an amino acid residue in a polypeptide of interest. Those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids.

As used herein, the terms "dosage form" and "unit dosage form" refer to a physically discrete unit of a therapeutic protein (e.g., antibody) for the patient to be treated. Each unit contains a predetermined quantity of active material calculated to produce the desired therapeutic effect. It will be understood, however, that the total dosage of the composition will be decided by the attending physician within the scope of sound medical judgment.

A "dosing regimen" (or "therapeutic regimen"), as that term is used herein, is a set of unit doses (typically more than one) that are administered individually to a subject, typically separated by periods of time. Preferably, a given therapeutic agent has a recommended dosing regimen, which may involve one or more doses. Preferably, a dosing regimen comprises a plurality of doses each of which are separated from one another by a time period of the same length; preferably, a dosing regimen comprises a plurality of doses and at least two different time periods separating individual doses. Preferably, all doses within a dosing regimen are of the same unit dose amount. Preferably, different doses within a dosing regimen are of different amounts. Preferably, a dosing regimen comprises a first dose in a first dose amount, followed by one or more additional doses in a second dose amount different from the first dose amount. Preferably, a dosing regimen comprises a first dose in a first dose amount, followed by one or more additional doses in a second dose amount same as the first dose amount.

As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. Preferably, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; plain water, isotonic saline; Ringer's solution; ethyl alcohol; pH buffered solutions; polyesters, polycarbonates and/or polyanhydrides; and other non-toxic compatible substances employed in pharmaceutical formulations.

As used herein, the term "pharmaceutical composition" refers to an active agent, formulated together with one or more pharmaceutically acceptable carriers. Preferably, active agent is present in unit dose amount appropriate for administration in a therapeutic regimen that shows a statistically significant probability of achieving a predetermined therapeutic effect when administered to a relevant population. Preferably, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

An individual who is "susceptible to" a disease, disorder, or condition (e.g., an infection by a dengue virus, or "DV") is at risk for developing the disease, disorder, or condition. Preferably, an individual who is susceptible to a disease, disorder, or condition does not display any symptoms of the disease, disorder, or condition. Preferably, an individual who is susceptible to a disease, disorder, or condition has not been diagnosed with the disease, disorder, and/or condition. Preferably, an individual who is susceptible to a disease, disorder, or condition is an individual who has been exposed to conditions associated with development of the disease, disorder, or condition (e.g., the individual has been exposed to DV). Preferably, a risk of developing a disease, disorder, and/or condition is a population-based risk (e.g., intravenous drug users; recipients of donated blood, blood products, and organs prior to 1992, when such products began to be screened; healthcare workers handling needles; babies born to DV-infected mothers; etc.).

According to the present invention, "symptoms are reduced" when one or more symptoms of a particular disease, disorder or condition is reduced in magnitude (e.g., intensity, severity, etc.) or frequency. For purposes of clarity, a delay in the onset of a particular symptom is considered one form of reducing the frequency of that symptom. To give but a few examples, exemplary symptoms of DV include, but are not limited to, sudden onset of fever, high fever (often over 40° C.), muscle and joint pains, headache, vomiting, diarrhea, occurrence of a rash as flushed skin or measles-like rash, petechiae (small red spots caused by broken capillaries that do not disappear when skin is pressed), bleeding from the mucous membranes, low white blood cell count, low platelets, metabolic acidosis, elevated level of aminotransferase from the liver, plasma leakage resulting in hemoconcentration (indicated by a rising hematocrit) and hypoalbuminemia, fluid accumulation in the chest and abdominal cavity (e.g., pleural effusion or ascites), gastrointestinal bleeding, shock and hemorrhage, positive tourniquet test, hypotension, infection of the brain or heart, impairment of vital organs (e.g., liver), neurological disorders such as transverse myelitis, and/or combinations thereof. It is not intended that the present invention be limited only to cases where the symptoms are eliminated. The present invention specifically contemplates treatment such that one or more symptoms is/are reduced (and the condition of the subject is thereby "improved"), albeit not completely eliminated.

As used herein, the phrase "therapeutic agent" refers to any agent that elicits a desired pharmacological effect when administered to an organism. Preferably, an agent is considered to be a therapeutic agent if it demonstrates a statistically significant effect across an appropriate population. Preferably, the appropriate population may be a population of model organisms. Preferably, an appropriate population may be defined by various criteria, such as a certain age group, gender, genetic background, preexisting clinical conditions, etc. Preferably, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

As used herein, the term "therapeutically effective amount" refers to an amount of a therapeutic protein which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

As used herein, the term "treatment" (also "treat" or "treating") refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition (e.g., DV). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. Preferably, treatment may be of a subject who has been diagnosed as suffering from the relevant disease, disorder, and/or condition. Preferably, treatment may be of a subject known to have one or more susceptibility factors that are statistically correlated with increased risk of development of the relevant disease, disorder, and/or condition.

The expression "unit dose" as used herein refers to an amount administered as a single dose and/or in a physically discrete unit of a pharmaceutical composition. Preferably, a unit dose contains a predetermined quantity of an active agent. Preferably, a unit dose contains an entire single dose of the agent. Preferably, more than one unit dose is administered to achieve a total single dose. Preferably, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, preferably, a total appropriate daily dosage of a particular therapeutic agent may comprise a portion, or a plurality, of unit doses, and may be decided, for example, by the attending physician within the scope of sound medical judgment. Preferably, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

As used herein, the term "vaccination" refers to the administration of a composition intended to generate an immune response, for example to a disease-causing agent. For the purposes of the present invention, vaccination can be administered before, during, and/or after exposure to a disease-causing agent, preferably, before, during, and/or shortly after exposure to the agent. Preferably, vaccination includes multiple administrations, appropriately spaced in time, of a vaccinating composition.

The present invention provides "matched antibody pairs" comprising the novel monoclonal antibodies of the invention wherein each matched pair of antibodies is capable of detecting and distinguishing between dengue virus NS1 protein serotypes DV1, DV2, DV3 and DV4 in an appropriate immunoassay. Preferably each matched antibody pair of the invention does also not cross react with the any proteins including the NS1 proteins of closely related viruses such as Zika virus and yellow fever virus. The invention also provides kits comprising one or more of the matched antibody pairs of the invention for use in appropriate sandwich immunoassays for testing biological samples for the presence of dengue virus. The invention also provided methods for identifying matched antibody pairs that are highly specific for not more than one serotype of dengue virus NS1 protein and which preferably do not cross react with the proteins of Zika virus and which preferably do not cross react with proteins of yellow fever virus. For clarity, one or both antibodies of a matched pair individually can bind more than one NS1 protein sequence. It is the combination or pair of antibodies that bind a single DV NS1.

There are a variety of assay formats known to those of ordinary skill in the art for using antibodies to detect an antigen in a sample which can be effectively employed in the disclosed methods. See, e.g., Harlow and Lane, Antibodies: A Laboratory Manual, Cold Spring Harbor Laboratory, 1988. Preferably, the assay is similar to an enzyme linked immunosorbent assay (ELISA)-sandwich assay, preferably in a lateral flow format. In this assay, an anti-dengue NS1 protein antibody of the invention referred to herein as the "detection antibody" which is labelled with a detection reagent such as a colorimetric label placed such as by pipetting on a membrane such as nitrocellulose. A biological sample that may contain dengue virus is applied to or otherwise contacted with the membrane to which the detection antibody is present. The biological sample migrates along the membrane through a region containing the detection antibody wherein the detection antibody binds a specific epitope of the NS1 protein of the dengue virus if such protein is present in the biological sample. The complex of the detection antibody with its bound antigen then migrates to the test area where a second antibody of the invention, referred to herein as the "capture antibody" is immobilized and binds to a different epitope of NS1 complex thereby forming a sandwich of the detection antibody, antigen and capture antibody. Concentration of detection reagent at the test area indicates the presence of dengue NS1 of a specific serotype in the sample, Such tests can typically be performed with a very small amount of biological sample.

An assay as described herein may in principle involve more than a matched pair of monoclonal antibodies such as is the case when multiplexing the detection of more than one dengue virus NS1 protein serotype with a mixture of capture antibodies in a single membrane detection area. Preferably, the method for detecting one or more serotypes of dengue virus in a sample or subject employs more than one matched antibody pair of the invention in a multiplexed lateral flow assay (LFA) such as that described in U.S. application Ser. No. 15/041,788, entitled Multiplexed Lateral Flow Assay to Hamad-Schifferli et al., filed on Feb. 11, 2016.

To be effective in an assay for detecting one or more serotypes of dengue virus, a matched antibody pair of the invention should be present in an amount sufficient to permit significant binding to the antigen. In order to obtain such amounts of bound antigen, the precise amount of each antibody may vary widely depending upon its affinity for the antigen so that lesser amounts of antibodies having higher affinities are required than of antibodies having lower affinities. Methods of measuring antibody affinity for an antigen are known in the art.

Preferred novel monoclonal antibodies useful in one or more matched pairs in accordance with the invention include, but are not limited to antibody (Ab) 55, antibody (Ab) 271, antibody (Ab) 323, antibody (Ab) 411, and antibody (Ab) 626. These antibodies were identified as being useful in a matched pair specific for only one serotype of dengue virus NS1 protein and as a matched pair, not cross reacting with other serotypes of dengue virus using methods of the invention for screening and selecting matched antibody pairs. The epitope peptide sequences of the NS1 protein recognized by each of antibodies 55, 271, 323, 411, and 626 are found in Table 2 and shown in FIG. 10.

Preferred novel monoclonal antibodies useful in one or more matched pairs in accordance with the invention include, but are not limited to antibody (Ab) 1, antibody (Ab) 164, antibody (Ab) 243, antibody (Ab) 850, and antibody (Ab) 912. These antibodies were identified as being useful in a matched pair specific for only one serotype of dengue virus NS1 protein and as a matched pair, not cross reacting with other serotypes of dengue virus using methods of the invention for screening and selecting matched antibody pairs. The epitope peptide sequences of the NS1 protein recognized by each of antibodies 1, 243 and 912 are provided in Table 2.

At least one of the antibodies of the matched antibody pairs described herein is preferably labeled with standard detectable markers, such as chemiluminescent detection systems, radioactive labels such as $^{125}I$, and enzymes such as horseradish peroxidase, biotin, and avidin. Preferably, suitable labels include gold nanoparticles, colored latex beads, magnetic particles, carbon nanoparticles, selenium nanoparticles, silver nanoparticles, quantum dots, up converting phosphors, organic fluorophores, textile dyes, enzymes, liposomes.

Any detectable label recognized in the art as being useful in various assays could be used in the present invention. In particular, the detectable label component can include compositions detectable by spectroscopic, photochemical, biochemical, immunochemical, or chemical means. The label component thus produces a detectable signal. Exemplary labels include fluorescent dyes, chemiluminescent compounds, radioisotopes, electron-dense reagents, enzymes, or colored particles (such as a metal sol or colloid, preferably gold). The label component can generate a measurable signal, such as radioactivity, fluorescent light, color, or enzyme activity, which can be used to identify and quantify the amount of label bound to a test site. Thus, the label component can also represent the presence of a particular antigen bound thereto.

A suitable label depends on the intended detection methods. The label can be a direct label or an indirect label. A direct label can be detected by an instrument, device or naked eyes without further step to generate a detectable signal. A visual direct label, e.g., a gold or latex particle label, can be detected by naked eyes. An indirect label, e.g., an enzyme label, requires further step to generate a detectable signal. Preferably, the label is a soluble label, such as a colorimetric, radioactive, enzymatic, luminescent or fluorescent label. Depending on the specific configurations, the labels such as colorimetric, radioactive, enzymatic, luminescent or fluorescent label, can be either a soluble label or a particle or particulate label.

Preferably, the detectable label having a unique spectral emission includes, but is not limited to, noble metal nanoparticles (NP) such as gold or silver nanoparticles, colored latex beads, magnetic particles, carbon nanoparticles, selenium nanoparticles, quantum dots, up converting phosphors, organic fluorophores and enzymes. Preferably the detectable labels provide a direct spectral signal at the completion of the assay such as the color detectable color from metal nanoparticles. Color release from an enzyme conversion for example requires an extra step to produce a spectral signature which is preferably avoided.

One or more of the matched antibody pairs of the present invention may be used to detect and distinguish between one or more serotypes of dengue virus found in a biological sample. The detection of one or more serotypes of dengue virus in a patient enables a clinician to treat the patient with one or more of the correct vaccines, for example that are specific to one or more of the serotypes of dengue virus found in the patient. Accurate diagnosis of dengue fever is critical to management of individual patients, and allows for appropriate infection control interventions such as quarantine and institution of outbreak procedures. One of the unusual aspects of dengue is that in some cases, the second infection has disease symptoms that are much more severe and can be life threatening. Primary infection results in dengue fever, where symptoms are fever, joint and muscle pain, aches, nausea, and a skin rash. Patients usually recover within 10 days and are immune to that particular serotype. However, patients infected with another serotype of dengue (secondary infection) are at a much higher risk for dengue hemorrhagic fever, which can result in much more serious complications, such as severe bleeding, and patients become at risk for dengue shock syndrome. This is a life threatening condition and typically only supportive care can be offered. Thus, the ability to distinguish between what serotype a patient is infected with is critical in determining whether or not they are at risk for dengue hemorrhagic fever or dengue shock syndrome.

From a public health point of view, the use of matched antibody pairs of the invention in the kits and methods of the invention can distinguish serotypes would be useful in knowing when a population is at risk for a hemorrhagic fever outbreak. For example, when two different serotypes have entered the same geographical the compositions and methods of the invention would be able to map incoming and provide understanding of the geographic distribution of viruses associated with hemorrhagic fever. If a region is already hyper-endemic and the four serotypes circulate simultaneously the methods of the present invention can explore the dynamics of virus infection and provide unique data on prevalence of one serotype over the other. The virus serotype dynamic is very important aspect of vaccination efforts, in this new phase of dengue vaccination with a tetravalent vaccine, equal protection for each of the four serotypes could be address utilizing the matched antibody pairs of the invention as a component of the epidemiological surveillance.

One preferred monoclonal antibody pair used as capture and detection antibodies in a sandwich immunoassay is Ab 271 paired with Ab 912 (271/912) for detecting dengue virus NS1 protein serotype 1 (DV1) (FIGS. 1 and 2).

One preferred monoclonal antibody pair used as capture and detection antibodies in a sandwich immunoassay is Ab 1 paired with Ab 164 (1/164) for detecting dengue virus NS1 serotype 2 (DV2) (FIGS. 1 and 2). Another preferred antibody pair for capture and detection of dengue NS1 serotype 2 (DV2) are Ab 850 paired with Ab 243 (850/243).

Figure 4:
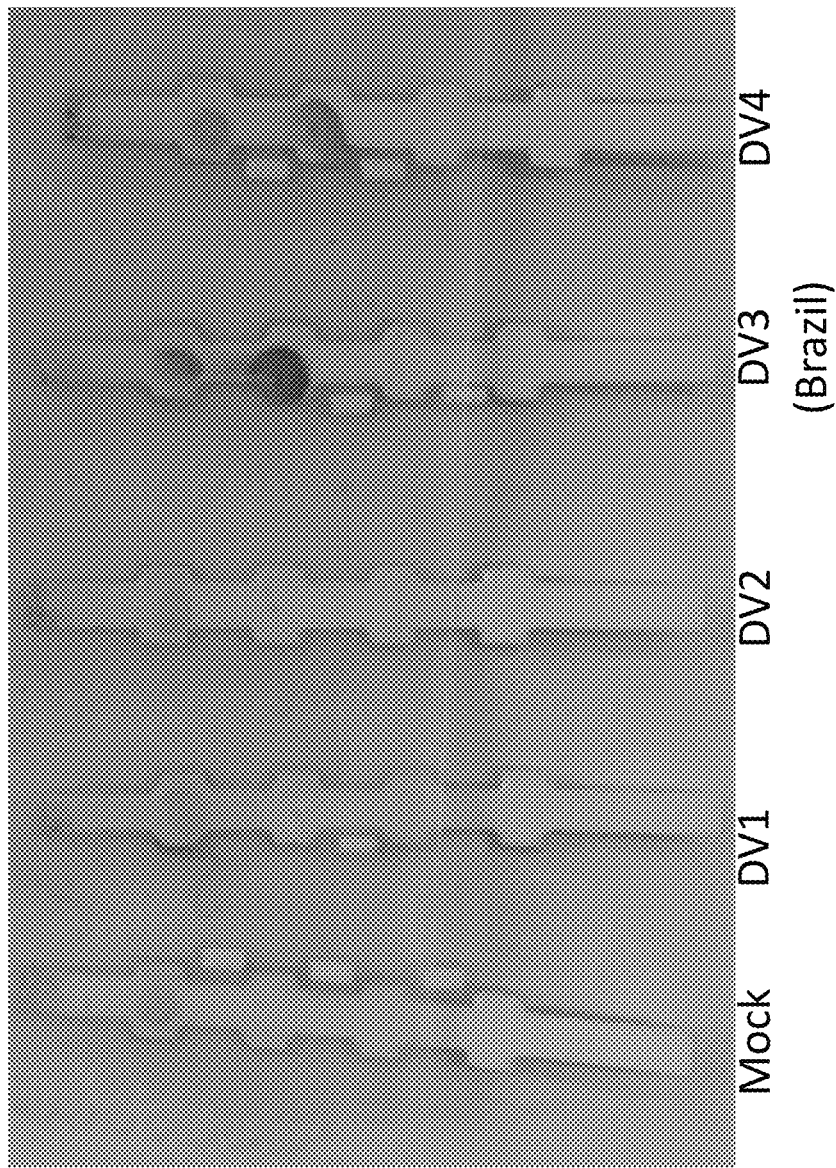
FIG. 4 shows experimental data from lateral flow assays indicating that the 725-323/725-55 antibody pair detects NS1 serotypes 3 and 4, but not 1 and 2. This pair is reversible.
Figure 5:
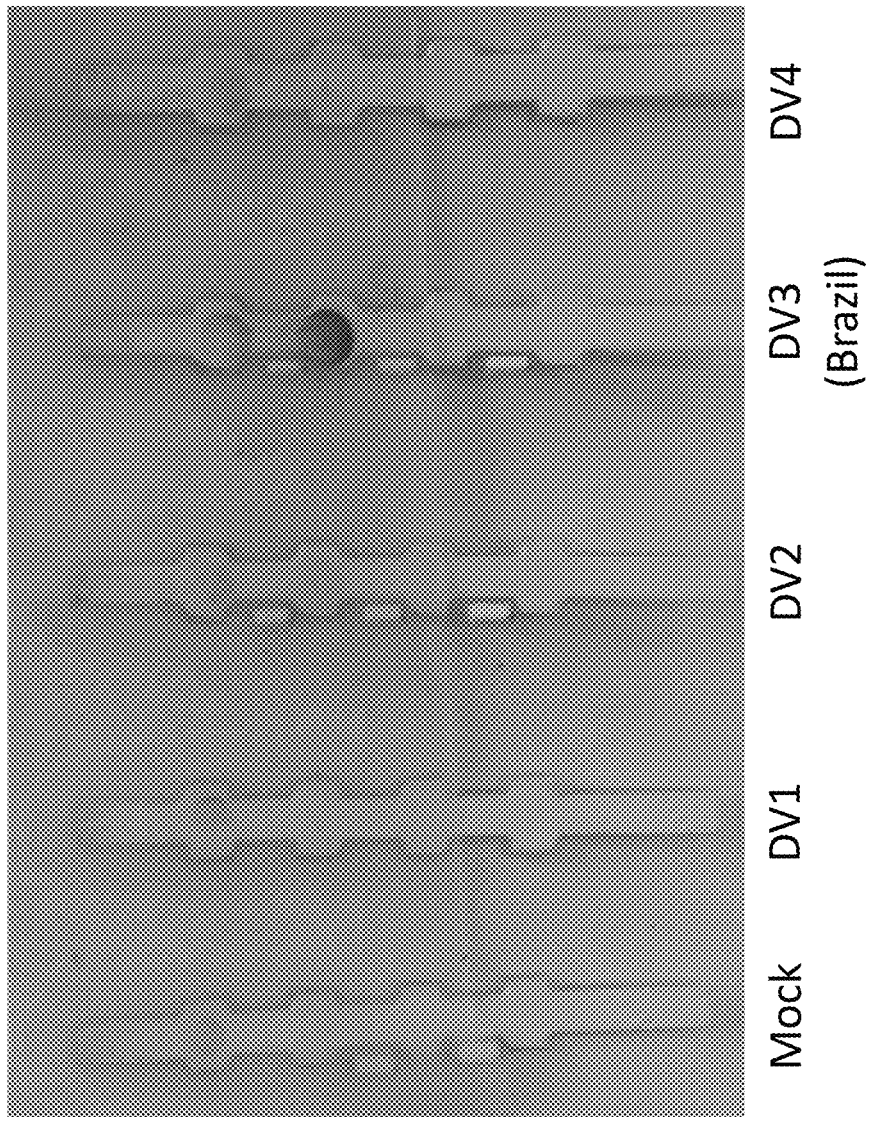
FIG. 5 shows experimental data from lateral flow assays indicating that the 725-323/725-411 antibody pair is specific for dengue serotype 3 (Brazil="Americas") and recombinant NS1 (serotype 3) protein from The Native Antigen Company (UK). This pair is reversible.

One preferred monoclonal antibody pair used as capture and detection antibodies in a sandwich immunoassay is Ab 55 paired with Ab 411 (55/411) for detecting dengue NS1 serotype 3 (DV3) (FIG. 3). Another preferred antibody pair for capture and detection of dengue NS1 serotype 3 (DV3) is Ab 323 paired with Ab 55 (323/55) (FIG. 4). Another preferred antibody pair for capture and detection of dengue NS1 serotype 3 (Dv3) is Ab 323 paired with Ab 411 (323/411) (FIG. 5).

Figure 6:
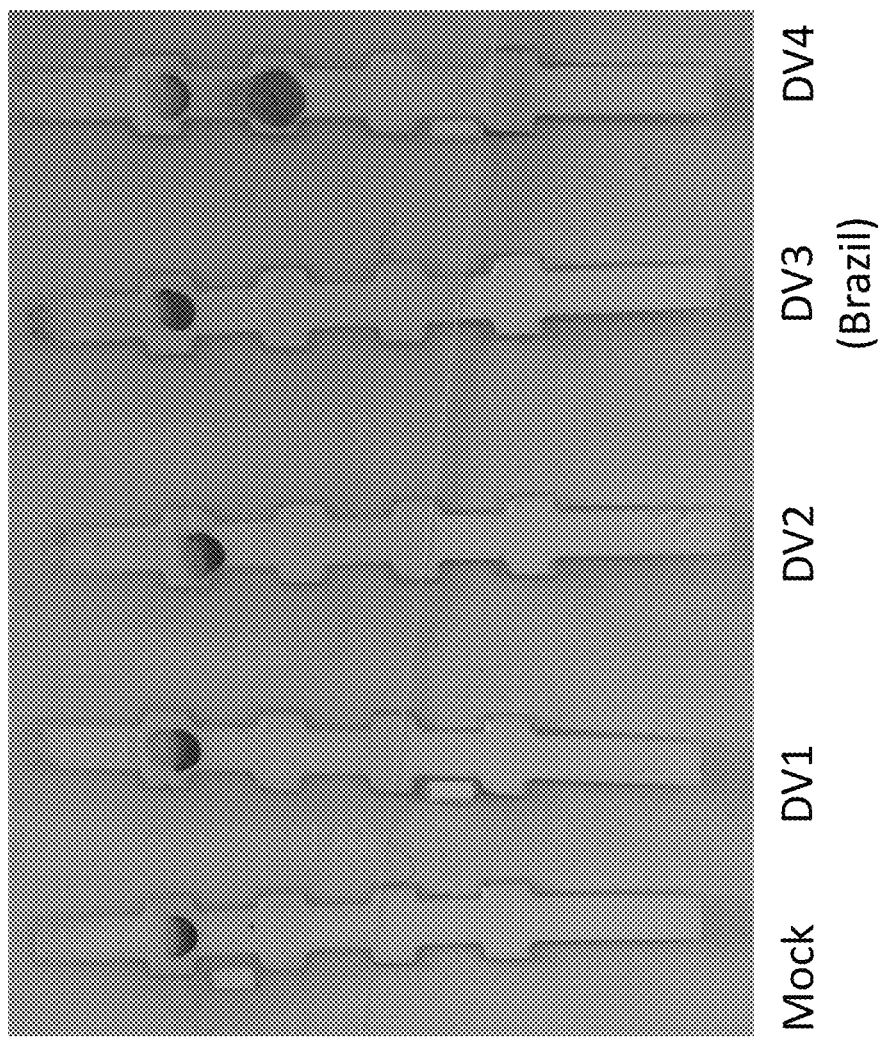
FIG. 6 shows experimental data from lateral flow assays indicating that the 725-323/724-626 pair is specific for dengue virus 4. This pair is reversible.
Figure 7:
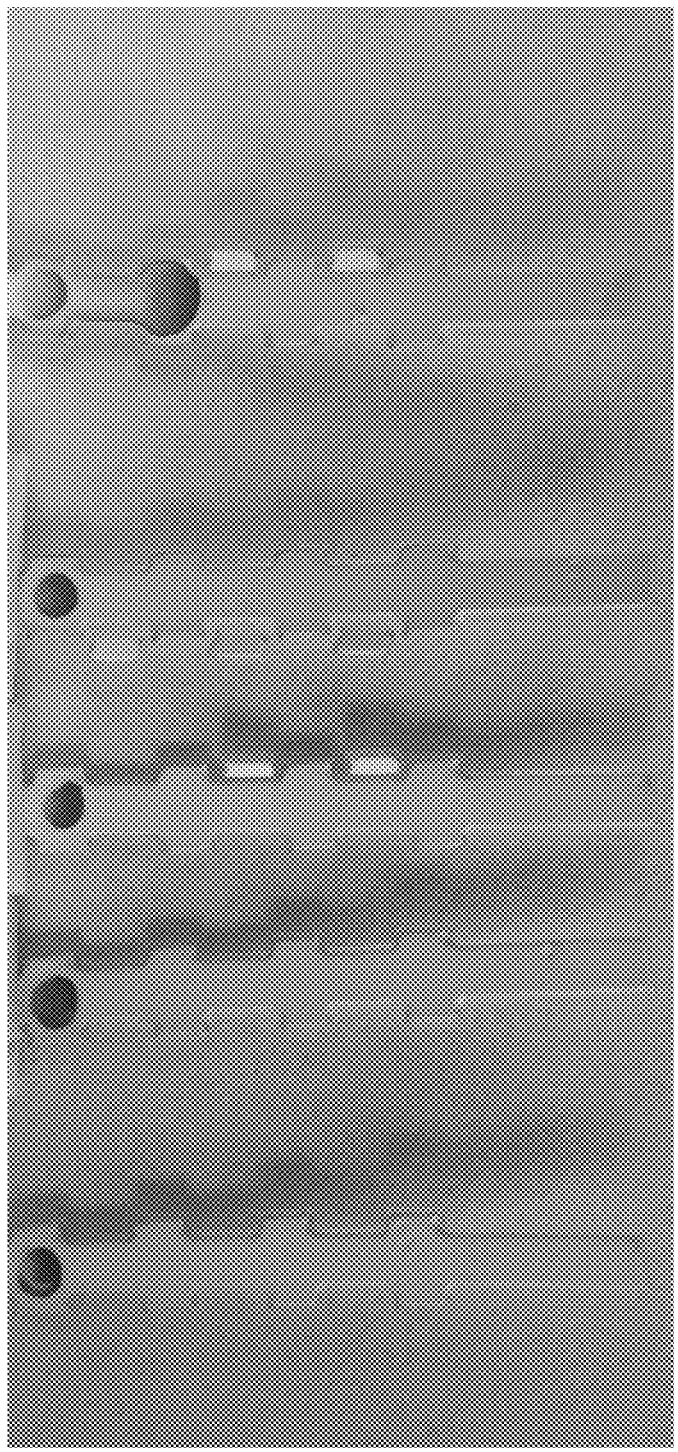
FIG. 7 shows experimental data from lateral flow assays indicating that the 724-626/725-55 pair is specific for the dengue virus serotype 4 NS1 protein. This pair is reversible.
Figure 8:
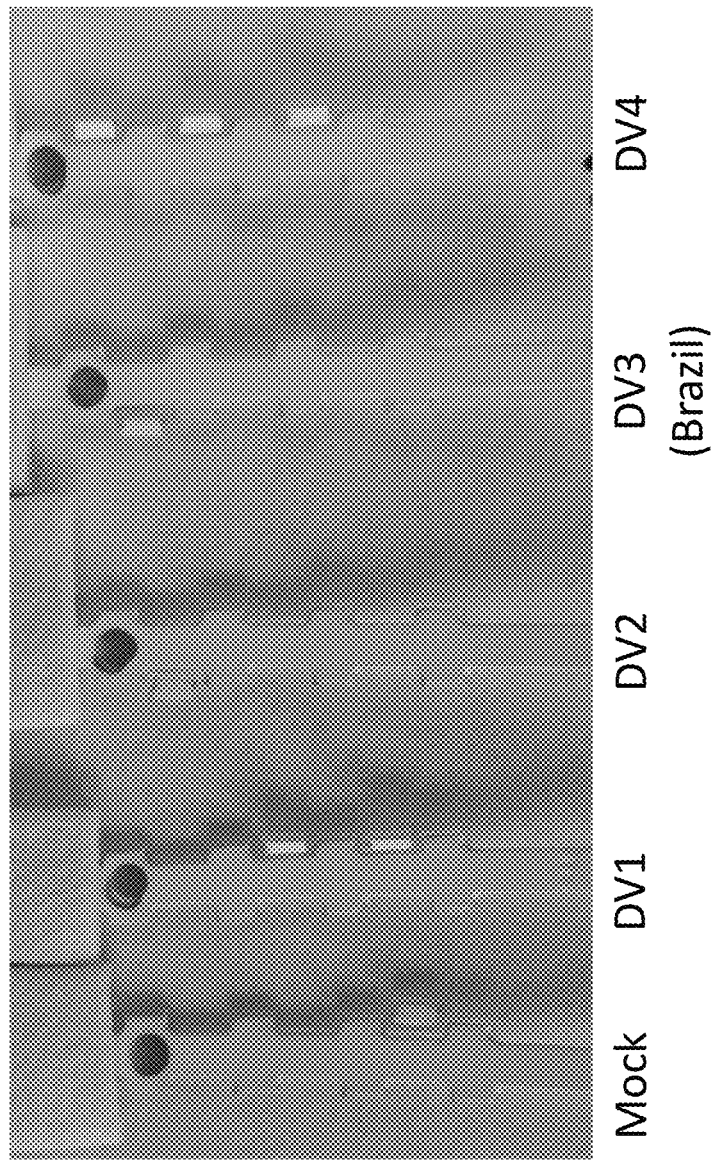
FIG. 8 shows experimental data from lateral flow control assays indicating that the 724-626/725-411 pair does not detect any of the dengue serotype NS1 proteins.
Figure 9:
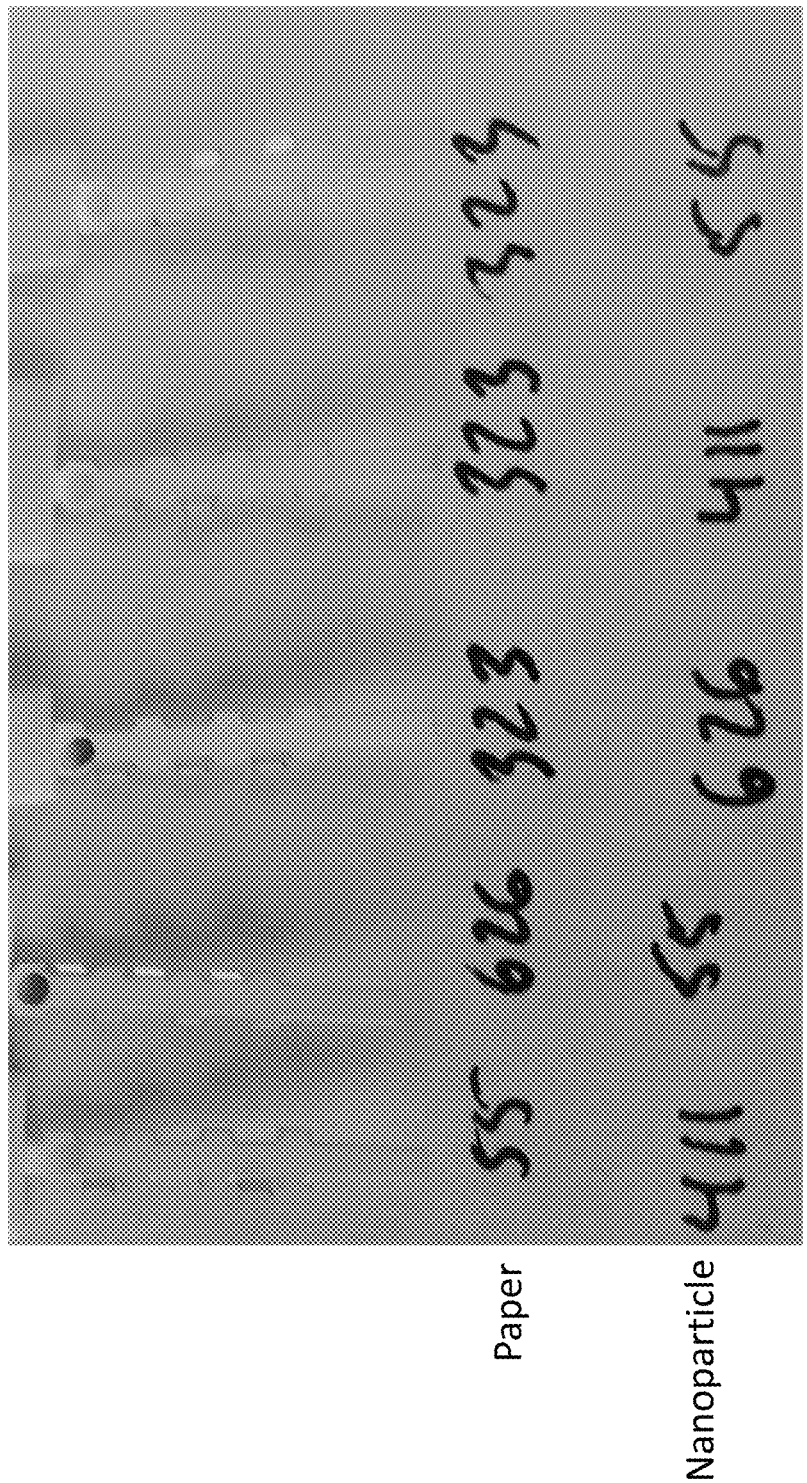
FIG. 9 shows experimental data from lateral flow assays indicating that the antibody pairs indicated in the figure do not cross react with purified yellow fever virus recombinant NS1 protein purchased from the Native Antigen Company (UK).
Figure 11:
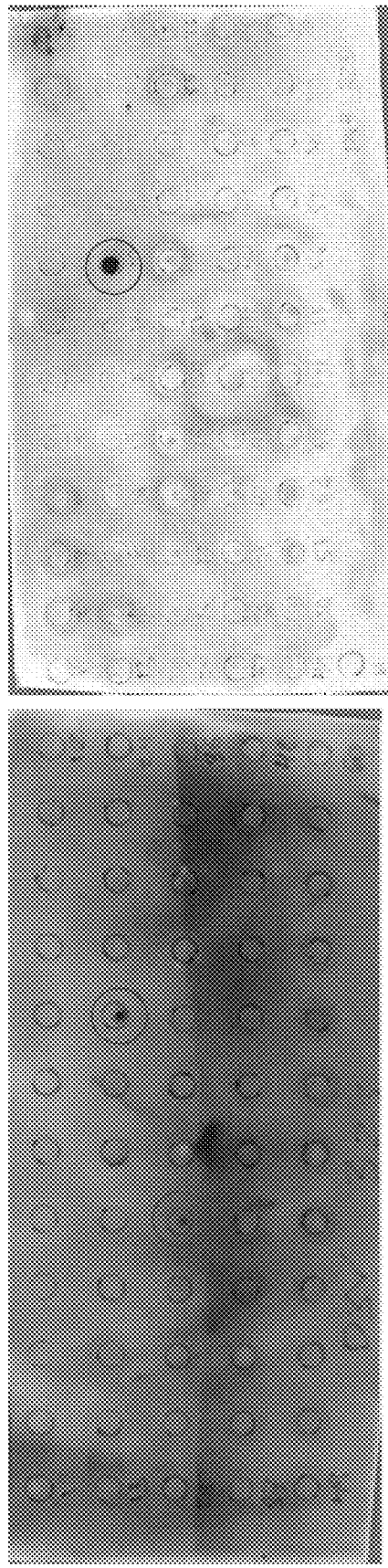
FIG. 11 shows peptides recognized by antibody 323 in peptide screening assay.
Figure 12:
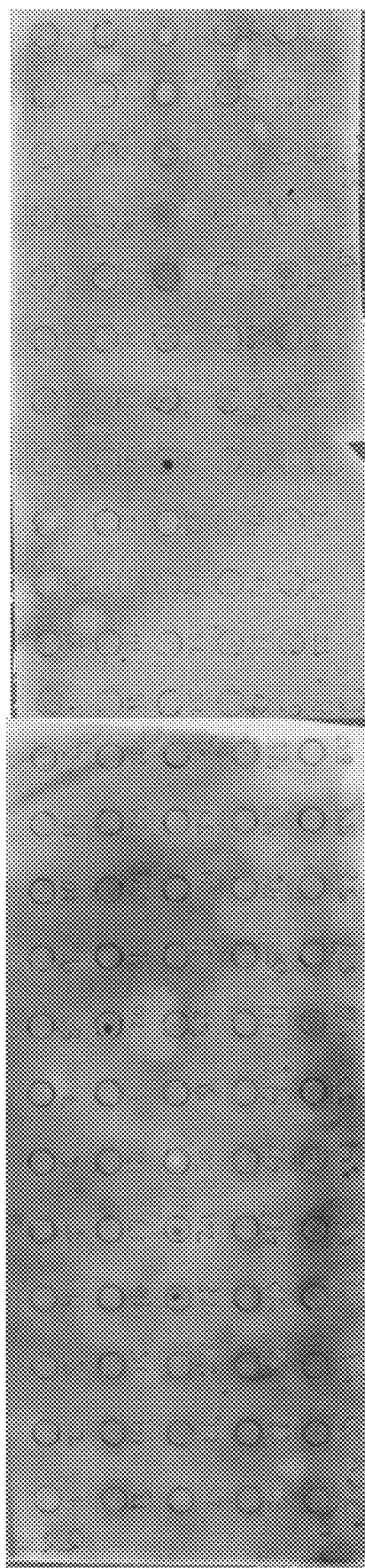
FIG. 12 shows peptides recognized by antibody 55 in peptide screening assay.
Figure 13:
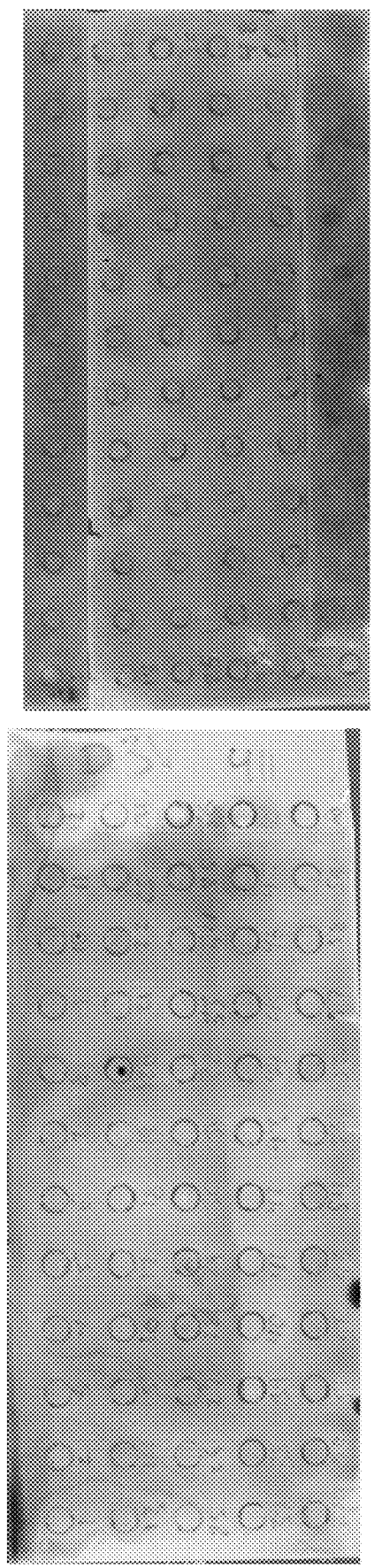
FIG. 13 shows peptides recognized by antibody 411 in peptide screening assay.
Figure 16:
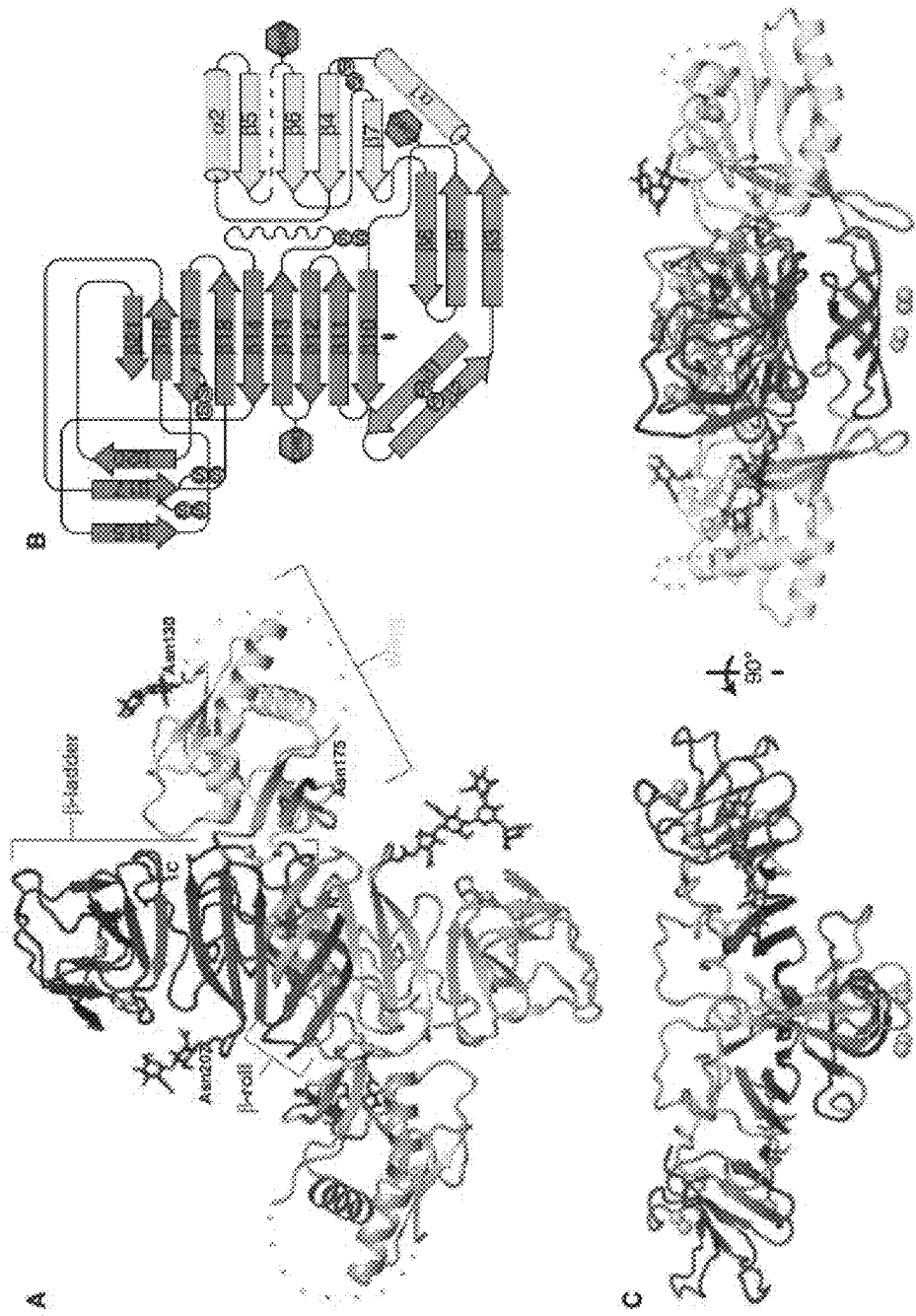
FIG. 16 is a schematic showing the structure of the NS1 protein.
Figure 17:
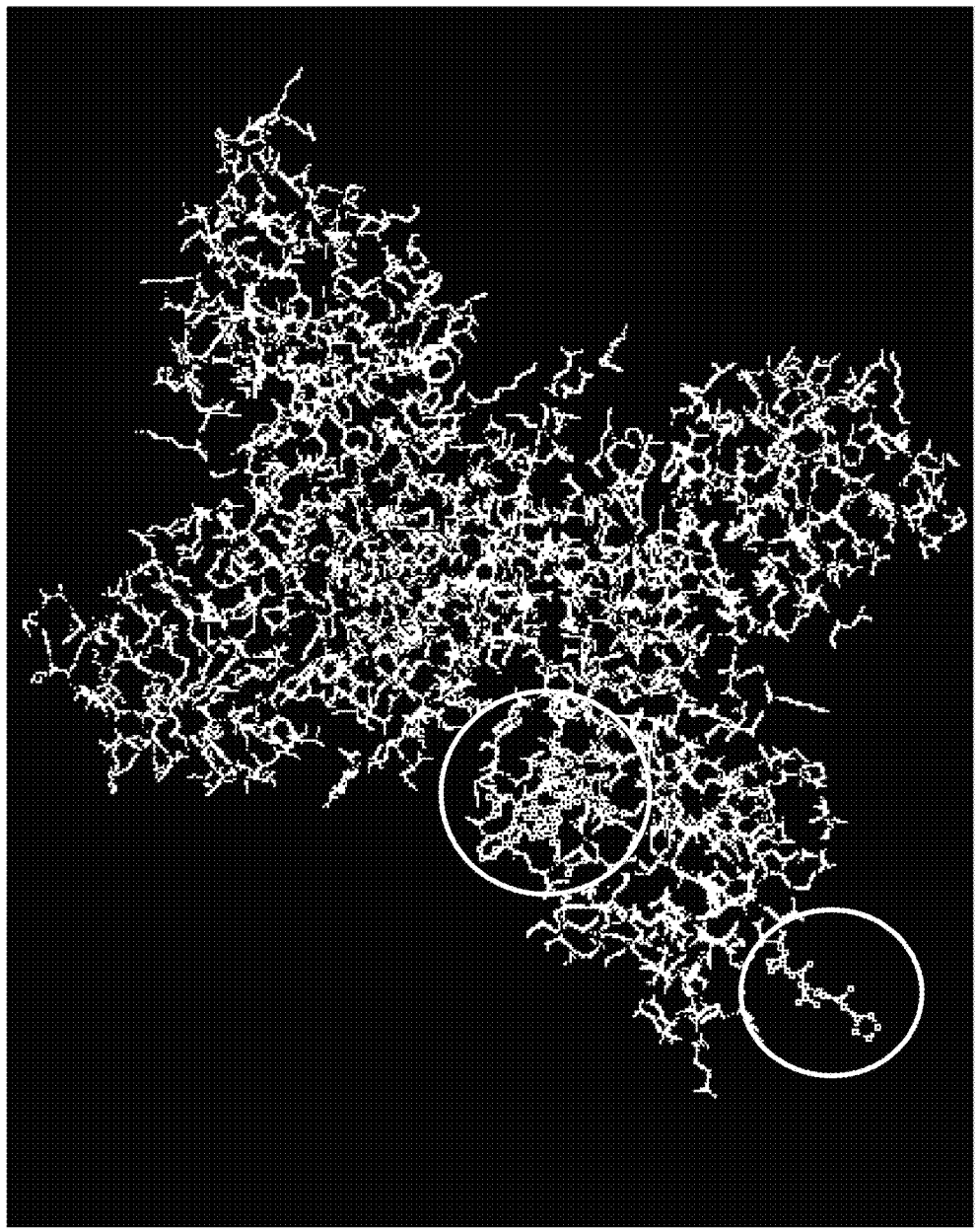
FIG. 17 is schematic showing the approximate location of peptides 20 and 29 on the dengue virus NS1 protein.

One preferred monoclonal antibody pair used as capture and detection antibodies in a sandwich immunoassay is Ab 323 paired with Ab 626 (323/626) (FIG. 6) for detecting dengue NS1 serotype 4 (DV4). Another preferred antibody pair for capture and detection of dengue NS1 serotype 4 (DV4) is Ab 626 paired with Ab 55 (626/55) (FIG. 7).

The nucleotide sequence and amino acid sequence of antibody 55 is found in FIG. 18. The nucleotide sequence and amino acid sequence of antibody 271 is found in FIG. 19. The nucleotide sequence and amino acid sequence of antibody 323 is found in FIG. 20. The nucleotide sequence and amino acid sequence of antibody 411 is found in FIG.

21. The nucleotide sequence and amino acid sequence of antibody 626 is found in FIG. 22. The invention includes antibodies that are at least 90% identical, preferably at least 95% identical and preferably at least 99% identical to the amino acid sequences of antibodies 55, 271, 323, 411, or 626.

The antibody pairs of the invention preferably do not cross react with the proteins of zika virus. Preferably, the matched antibody pairs of the invention also do not cross react with the proteins of yellow fever virus.

The "half strip format" (also referred to herein as a dipstick) along with lateral flow assay formats are among the examples in which the antibodies described herein are utilized to detect dengue virus infection. In addition to using specific pairs of antibodies to distinguish among the serotypes of dengue, the combination of antibodies can also be utilized to detect any of the serotypes (Pan-dengue detection).

Preferably, the antibodies of the invention are also useful for binding to the natural ligands (NS1 present in serum, or body fluids, or cell infected supernatants) which are attached to solid surfaces, such as a microtiter plate with wells. The antibody specific for a specific dengue serotype NS1 protein can be immobilized and incubated appropriately with a secondary anti-mouse antibody with various enzymatic ligands. These detector antibodies will bind to the NS1 antibodies described in this invention, and a detectable signal further generated is then interpreted as the amount of NS1 contained in the original sample. This type of technique known as indirect ELISA, in the presence of additional negative controls, positive controls, and cut-off controls; and/or appropriate buffers can be utilized as a way to determine numerically the initial amount of NS1 protein in a given sample.

Preferably, the antibodies of the invention are also useful in a flow cytometry assay or immunofluorescence assay. The use of the antibodies in detecting a cell infected with dengue virus is an alternative application by which cells that are infected in vivo or in vitro are utilized in an assay in combination with the antibodies of the invention. The cells can be fixed and permeabilized according to protocols and incubated with an appropriate amount of antibody, sufficient to bind to the target NS1 inside and on the surface of infected cells. The positive signal is recognized by a secondary anti-mouse antibody that detects in a proportional manner the intensity of a fluorescent light and by means of the use of flow cytometric detection of immunofluorescence detection, the number and proportion of infected cells is obtained as a result of this assay.

The matched antibody pairs of the present invention may be presented in kits with optional detectable labels and other reagents such as positive or negative controls and buffers for such detection. Preferably the kit includes at least one matched antibody pair of the invention. Preferably one of the antibodies of the matched antibody pair is labeled for example, with a colorimetric detection label. The labelled antibody may preferably be present in a vial to which biological sample and appropriate buffers are added in order to allow for the labelled detection antibody to complex with any target antigen that is present in the sample. Alternatively, the labelled antibody may be bound to, for example, the appropriate location on an assay strip such as that described in U.S. application Ser. No. 15/041,788, entitled Multiplexed Lateral Flow Assay to Hamad-Schifferli et al., filed on even date herewith and incorporated herein by reference. Preferably the capture antibody is bound to an assay strip or alternatively may be present in its own vial until used in an appropriate immunoassay. The kit may further comprise a container with a positive control, a negative control, or sample diluent if appropriate. Alternatively, the controls may be bound to an appropriate assay strip such as that described in U.S. application Ser. No. 15/041,788, entitled Multiplexed Lateral Flow Assay to Hamad-Schifferli et al., filed on even date herewith. Preferably, the kit also comprises additional reagents or buffers or medical equipment such as sterile syringes, for obtaining or collecting the sample, a container for holding and/or storing the sample. To use the kit of the invention, a biological sample is collected from a human such as human serum and then placed in contact with the labelled first antibody of the antibody pair for sufficient time and under conditions for any target antigen present in the serum to bind to the first antibody. The complex is then brought into contact with the second antibody of the antibody pair, preferably as the result of capillary action on the assay strip which draws the complex of the first detection antibody of the antibody pair in contact with the second capture antibody of the antibody pair resulting in the detectable binding between the first labelled detection antibody complexed with the antigen and the second capture antibody also bound to the antigen.

In addition to the use of the novel antibodies of the invention as matched antibody pairs for diagnostics and detection of specific dengue virus NS1 protein serotypes, one or more individual anti-dengue virus antibodies of the invention are also useful as therapeutic or prophylactic agents in the treatment of dengue virus. Preferably, antibodies of the invention are useful in the treatment of chronic and/or acute DV infection, for example by administering to a patient suffering from or susceptible to such infection a therapeutically effective amount of one or more antibodies of the invention. Preferably, a therapeutically effective amount is an amount sufficient to achieve one or more particular biological effects, including, but not limited to, (i) reducing severity or frequency of, and/or delaying onset or re-emergence of one or more symptoms or characteristics of DV infection in an individual susceptible to or suffering from DV infection; and/or (ii) reducing risk of infection and/or of development of one or more symptoms or characteristics of DV infection in an individual exposed or at risk of exposure to DV infection. Preferably, the one or more symptoms or characteristics of DV infection is or comprises high fever and at least one or more additional symptoms selected for example from severe headache, severe eye pain, joint pain, muscle pain, bone pain, rash, mild bleeding manifestation (e.g., nose or gum bleeding, easy bruising), abdominal pain, vomiting, black, tarry stools, drowsiness or irritability, pale, cold or clammy skin, difficulty breathing, low white cell count, circulating viral particles in an individual or one or more tissues (e.g., blood, bone marrow) or organs (e.g., liver) thereof. Preferably, an individual suffering from DV infection displays high fever and at least two such additional symptoms.

Preferably, the antibodies of the invention may be used to prevent, reduce recurrence of, and/or delay onset of one or more symptoms or characteristics of DV infection. Preferably antibodies of the invention may be used, for example, for passive immunization of individuals recently exposed to DV or at risk of being exposed to DV, newborn babies born to DV-positive mothers, and/or liver transplantation patients (e.g., to prevent possible recurrent DV infections in such patients).

Preferably, the present invention provides therapeutic methods of treatment, utilized after development of one or more symptoms of DV infection. Preferably, the present invention provides therapeutic methods of prophylaxis, utilized prior to development of one or more symptoms of DV infection, and/or prior to exposure to DV, DV infection, or risk thereof. The present invention also provides passive immunization technologies. Preferably, anti-dengue antibodies of the invention are combined with one or more additional pharmaceutically acceptable substances to provide pharmaceutical compositions. The present invention provides pharmaceutical compositions for treatment, prevention, diagnosis and/or characterization of DV infection.

Preferably, anti-dengue antibodies of the invention may be utilized together with one or more other therapies for treating, reducing incidence, frequency, or severity of, and/or delaying onset of DV infection or one or more symptoms or characteristics thereof. For example, preferably, anti-dengue antibodies of the invention are utilized together with one or more anti-viral agents, anti-inflammatories, pain relievers, immunomodulating therapeutics and combination therapy, which preferably involves other DV targets. For example, preferably, anti-dengue antibodies of the invention are administered in combination with one or more interferons (e.g., interferon α-2b, interferon-γ, etc.), analgesics (preferably containing acetaminophen and not aspirin and/or ibuprofen), anti-DV monoclonal antibodies, anti-DV polyclonal antibodies, RNA polymerase inhibitors, protease inhibitors, nucleoside analogs, helicase inhibitors, immunomodulators, antisense compounds, short interfering RNAs (siRNAs), short hairpin RNAs (shRNAs), micro RNAs (miRNAs), RNA aptamers, ribozymes, and combinations thereof.

Preferably, the invention provides an anti-dengue antibody whose heavy chain variable region and/or light chain variable region includes at least one complementarity determining region (CDR) sharing at least 80% sequence identity, preferably at least 90% sequence identity, preferably at least 95% sequence identity and preferably at least 99% sequence identity, with a CDR of reference antibody (Ab) 55 shown in FIG. 18. Preferably the sequence differs by substitution of at least one amino residue within the reference at least one CDR of Ab 55 of FIG. 18. Preferably, the antibody includes at least one CDR that is substantially identical to at least one reference CDR of Ab 55 in that it is either identical to such reference CDR or includes between 1-5 substitutions of amino acids within such reference CDR. Preferably, the antibody includes at least one heavy chain CDR that is substantially identical to at least one heavy chain reference Ab 55 CDR and also includes at least one light chain CDR that is identical to at least one light chain reference Ab 55 CDR. Preferably, each of the CDRs in the antibody is substantially identical to at least one of the reference CDRs of Ab 55 of FIG. 18.

Preferably, the invention provides an anti-dengue antibody whose heavy chain variable region and/or light chain variable region includes at least one complementarity determining region (CDR) sharing at least 80% sequence identity, preferably at least 90% sequence identity, preferably at least 95% sequence identity and preferably at least 99% sequence identity, with a CDR of reference Ab 271 shown in FIG. 19. Preferably the sequence differs by substitution of at least one amino residue within the reference at least one CDR of Ab 271 of FIG. 19. Preferably, the antibody includes at least one CDR that is substantially identical to a reference CDR of reference Ab 271 in that it is either identical to such reference CDR or includes between 1-5 substitutions of amino acids within such reference CDR. Preferably, the antibody includes at least one heavy chain CDR that is substantially identical to at least one heavy chain reference Ab 271 CDR and also includes at least one light chain CDR that is identical to at least one light chain reference Ab 271 CDR. Preferably, each of the CDRs in the antibody is substantially identical to one of the reference CDRs of Ab 271 of FIG. 19.

Preferably, the invention provides an anti-dengue antibody whose heavy chain variable region and/or light chain variable region includes at least one complementarity determining region (CDR) sharing at least 80% sequence identity, preferably at least 90% sequence identity, preferably at least 95% sequence identity and preferably at least 99% sequence identity, with a CDR of reference antibody (Ab) 323 shown in FIG. 20. Preferably the sequence differs by substitution of at least one amino residue within the reference at least one CDR of Ab 323 of FIG. 20. Preferably, the antibody includes at least one CDR that is substantially identical to at least one reference CDR of Ab 323 in that it is either identical to such reference CDR or includes between 1-5 substitutions of amino acids within such reference CDR. Preferably, the antibody includes at least one heavy chain CDR that is substantially identical to at least one heavy chain reference Ab 323 CDR and also includes at least one light chain CDR that is identical to at least one light chain reference Ab 323 CDR. Preferably, each of the CDRs in the antibody is substantially identical to at least one of the reference CDRs of Ab 323 of FIG. 20.

Preferably, the invention provides an antibody whose heavy chain variable region and/or light chain variable region includes at least one complementarity determining region (CDR) sharing at least 80% sequence identity, preferably at least 90% sequence identity, preferably at least 95% sequence identity and preferably at least 99% sequence identity, with a CDR of reference antibody (Ab) 411 shown in FIG. 21. Preferably the sequence differs by substitution of at least one amino residue within the reference at least one CDR of Ab 411 of FIG. 21. Preferably, the antibody includes at least one CDR that is substantially identical to at least one reference CDR of Ab 411 in that it is either identical to such reference CDR or includes between 1-5 substitutions of amino acids within such reference CDR. Preferably, the antibody includes at least one heavy chain CDR that is substantially identical to at least one heavy chain reference Ab 411 CDR and also includes at least one light chain CDR that is identical to at least one light chain reference Ab 411 CDR. Preferably, each of the CDRs in the antibody is substantially identical to at least one of the reference CDRs of Ab 411 of FIG. 21.

Preferably, the invention provides an antibody whose heavy chain variable region and/or light chain variable region includes at least one complementarity determining region (CDR) sharing at least 80% sequence identity, preferably at least 90% sequence identity, preferably at least 95% sequence identity and preferably at least 99% sequence identity, with a CDR of reference antibody (Ab) 626 shown in FIG. 22. Preferably the sequence differs by substitution of at least one amino residue within the reference at least one CDR of Ab 626 of FIG. 22. Preferably, the antibody includes at least one CDR that is substantially identical to at least one reference CDR of Ab 626 in that it is either identical to such reference CDR or includes between 1-5 substitutions of amino acids within such reference CDR. Preferably, the antibody includes at least one heavy chain CDR that is substantially identical to at least one heavy chain reference Ab 626 CDR and also includes at least one light chain CDR that is identical to at least one light chain reference Ab 626

CDR. Preferably, each of the CDRs in the antibody is substantially identical to at least one of the reference CDRs of Ab 626 of FIG. 22.

Preferably, the invention provides an antibody which is an IgG. Preferably, an antibody is a monoclonal antibody. Preferably, an antibody is selected from the group consisting of: a mouse antibody, a humanized antibody, a human antibody, a purified antibody, an isolated antibody, a chimeric antibody, a polyclonal antibody, and combinations thereof. Preferably, an antibody is provided wherein the antigen binding fragment is selected from the group consisting of: a Fab fragment, a Fab' fragment, a F(ab')$_2$ fragment, a Fd fragment, a Fd' fragment, a Fv fragment, a dAb fragment, a scFv fragment, an isolated CDR region, a dsFv diabody, a single chain antibody, and combinations thereof.

Preferably, the invention provides a pharmaceutical composition including a therapeutically effective amount of one or more anti-dengue antibodies of the invention and a pharmaceutically acceptable excipient, wherein the pharmaceutical composition treats at least one dengue virus serotype infection in a patient. Preferably, a pharmaceutical composition further includes at least one additional antiviral agent.

Preferably, the invention provides methods of treating a subject in need thereof suffering from at least dengue virus serotype infection, including the step of administering a therapeutically effective amount of an anti-dengue antibody of the invention.

Preferably, the invention provides methods of manufacturing pharmaceutical compositions, the method including the steps of providing an anti-dengue antibody of the invention (e.g. Ab 55, Ab 271, Ab323, Ab 411, Ab 626, et al.) and formulating the antibody with at least one pharmaceutically acceptable carrier, so that a pharmaceutical composition is generated. Preferably, the pharmaceutical composition is a liquid composition. Preferably, the pharmaceutical composition is formulated for parenteral administration. Preferably, the pharmaceutical composition is formulated for intravenous administration. Preferably, the pharmaceutical composition is formulated for intravenous administration to a child. Preferably the pharmaceutical composition is formulated for oral administration.

Anti-dengue antibodies of the invention or portions thereof, or nucleic acids encoding them, may be produced by any available means. Methods for generating antibodies (e.g., monoclonal antibodies and/or polyclonal antibodies) are well known in the art. It will be appreciated that a wide range of animal species can be used for the production of antisera, including rabbit, mouse, rat, hamster, guinea pig or goat. The choice of animal may be decided upon the ease of manipulation, costs or the desired amount of sera, as would be known to one of skill in the art. It will be appreciated that antibody agent can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. Anti-dengue antibodies of the invention and/or portions thereof may be produced, for example, by utilizing a host cell system engineered to express an inventive antibody-encoding nucleic acid. Alternatively or additionally, anti-dengue antibodies may be partially or fully prepared by chemical synthesis (e.g., using an automated peptide synthesizer).

Exemplary sources of anti-dengue antibodies of the invention include, but are not limited to, conditioned culture medium derived from culturing a recombinant cell line that expresses a protein of interest, or from a cell extract of, e.g., antibody-producing cells, bacteria, fungal cells, insect cells, transgenic plants or plant cells, transgenic animals or animal cells, or serum of animals, ascites fluid, hybridoma or myeloma supernatants. Suitable bacterial cells include, but are not limited to, *Escherichia coli* cells. Examples of suitable *E. coli* strains include: HB101, DH5a, GM2929, JM109, KW251, NM538, NM539, and any *E. coli* strain that fails to cleave foreign DNA. Suitable fungal host cells that can be used include, but are not limited to, *Saccharomyces cerevisiae, Pichia pastoris* and *Aspergillus* cells. Suitable insect cells include, but are not limited to, S2 Schneider cells, D. Mel-2 cells, SF9, SF21, HIGH-5™, MIMIC™-SF9, MG1 and KC1 cells. Suitable exemplary recombinant cell lines include, but are not limited to, BALB/c mouse myeloma line, human retinoblasts (PER.C6), monkey kidney cells, human embryonic kidney line (293), baby hamster kidney cells (BHK), Chinese hamster ovary cells (CHO), mouse sertoli cells, African green monkey kidney cells (VERO-76), human cervical carcinoma cells (HeLa), canine kidney cells, buffalo rat liver cells, human lung cells, human liver cells, mouse mammary tumor cells, TR1 cells, MRC 5 cells, FS4 cells, and human hepatoma line (Hep G2).

Anti-dengue antibodies of the invention can be expressed using various vectors (e.g., viral vectors) known in the art and cells can be cultured under various conditions known in the art (e.g., fed-batch). Various methods of genetically engineering cells to produce antibodies are well known in the art. (See e.g., Ausabel et al., eds. (1990), Current Protocols in Molecular Biology (Wiley, New York)).

Anti-dengue antibodies may be purified, if desired, using filtration, centrifugation and/or various chromatographic methods such as HPLC or affinity chromatography. Preferably, fragments of anti-dengue antibodies are obtained by methods which include digestion with enzymes, such as pepsin or papain, and/or by cleavage of disulfide bonds by chemical reduction.

Anti-dengue antibody of the invention may themselves also be used to identify and/or to characterize other dengue virus-binding agents (e.g., antibodies, polypeptides, small molecules, etc.).

The present invention also provides nucleic acids which encode an anti-dengue antibody of the invention. Preferred nucleic acids of the anti-dengue antibodies of the invention are found in FIGS. 18-22. The invention also provides nucleic acids which are complementary to nucleic acids which encode an antibody agent.

The present invention provides pharmaceutical compositions comprising one or more anti-dengue antibodies of the invention (e.g. Ab 55, Ab 271, Ab323, Ab 411, Ab 626 et al.). Preferably the present invention provides at least one antibody of the invention and at least one pharmaceutically acceptable excipient. Such pharmaceutical compositions may optionally comprise and/or be administered in combination with one or more additional therapeutically active substances. Preferably, provided pharmaceutical compositions are useful as prophylactic agents (i.e., vaccines) in the treatment or prevention of one or more serotypes of DV infection or of negative ramifications associated or correlated with DV infection. Preferably, pharmaceutical compositions are useful in therapeutic applications, for example in individuals suffering from or susceptible to one or more serotypes of DV infection. Preferably, pharmaceutical compositions are formulated for administration to humans.

For example, pharmaceutical compositions provided herein may be provided in a sterile injectable form (e.g., a form that is suitable for subcutaneous injection or intravenous infusion). For example, preferably, pharmaceutical compositions are provided in a liquid dosage form that is suitable for injection. Preferably, pharmaceutical compositions are provided as powders (e.g. lyophilized and/or sterilized), optionally under vacuum, which are reconstituted with an aqueous diluent (e.g., water, buffer, salt solution, etc.) prior to injection. Preferably, pharmaceutical compositions are diluted and/or reconstituted in water, sodium chloride solution, sodium acetate solution, benzyl alcohol solution, phosphate buffered saline, etc. Preferably, powder should be mixed gently with the aqueous diluent (e.g., not shaken).

Preferably, provided pharmaceutical compositions comprise one or more pharmaceutically acceptable excipients (e.g., preservative, inert diluent, dispersing agent, surface active agent and/or emulsifier, buffering agent, etc.). Preferably, pharmaceutical compositions comprise one or more preservatives. Preferably, pharmaceutical compositions comprise no preservative.

Preferably, pharmaceutical compositions are provided in a form that can be refrigerated and/or frozen. Preferably, pharmaceutical compositions are provided in a form that cannot be refrigerated and/or frozen. Preferably, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer).

Liquid dosage forms and/or reconstituted solutions may comprise particulate matter and/or discoloration prior to administration. Preferably, a solution should not be used if discolored or cloudy and/or if particulate matter remains after filtration.

Formulations of the pharmaceutical compositions described herein may be prepared by any method known or hereafter developed in the art of pharmacology. Preferably, such preparatory methods include the step of bringing active ingredient into association with one or more excipients and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to a dose which would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active ingredient.

Pharmaceutical compositions of the present invention may additionally comprise a pharmaceutically acceptable excipient, which, as used herein, may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof.

It will be appreciated that an anti-dengue antibody of the invention (e.g., Ab 55, Ab 271, Ab 323, Ab 411, Ab 626, et al.) in accordance with the present invention and/or pharmaceutical compositions thereof can be employed in combination therapies. By "in combination with," it is not intended to imply that the agents must be administered at the same time and/or formulated for delivery together, although these methods of delivery are within the scope of the invention. Compositions can be administered concurrently with, prior to, or subsequent to, one or more other desired therapeutics or medical procedures. It will be appreciated that therapeutically active agents utilized in combination may be administered together in a single composition or administered separately in different compositions. In general, each agent will be administered at a dose and/or on a time schedule determined for that agent.

The particular combination of therapies (e.g., therapeutics or procedures) to employ in a combination regimen will take into account compatibility of the desired therapeutics and/or procedures and the desired therapeutic effect to be achieved. It will also be appreciated that pharmaceutical compositions of the present invention can be employed in combination therapies (e.g., combination vaccine therapies), that is, the pharmaceutical compositions can be administered concurrently with, prior to, or subsequent to, one or more other desired therapeutic and/or vaccination procedures.

Therapeutically effective amounts of anti-dengue antibodies in accordance with the invention combined with for use in combination with a provided pharmaceutical composition and at least one other active ingredient. Preferably, an active ingredient is an anti-viral agent, such as, but not limited to, interferons (e.g., interferon α-2b, interferon-γ, etc.), anti-DV monoclonal antibodies, anti-DV polyclonal antibodies, RNA polymerase inhibitors, protease inhibitors, helicase inhibitors, immunomodulators, antisense compounds, short interfering RNAs, short hairpin RNAs, micro RNAs, RNA aptamers, ribozymes, and combinations thereof. The particular combination of therapies to employ in a combination regimen will generally take into account compatibility of the desired therapeutics and/or procedures and the desired therapeutic effect to be achieved. It will also be appreciated that the therapies and/or vaccines employed may achieve a desired effect for the same disorder (for example, an inventive antigen may be administered concurrently with another DV vaccine), or they may achieve different effects.

It will be appreciated that the therapies employed may achieve a desired effect for the same purpose (for example, DV antibodies useful for treating, preventing, and/or delaying the onset of DV infection may be administered concurrently with another agent useful for treating, preventing, and/or delaying the onset of DV infection), or they may achieve different effects (e.g., control of any adverse effects). The invention encompasses the delivery of pharmaceutical compositions in combination with agents that may improve their bioavailability, reduce and/or modify their metabolism, inhibit their excretion, and/or modify their distribution within the body.

Preferably, agents utilized in combination with be utilized at levels that do not exceed the levels at which they are utilized individually. Preferably, the levels utilized in combination will be lower than those utilized individually.

Preferably, anti-dengue antibodies in accordance with the invention may be administered with interferon, with RNA polymerase inhibitors, or with both interferon and RNA polymerase inhibitors.

Preferably, combination therapy may involve administrations of a plurality of anti-dengue antibodies directed to different proteins of DV, for example to simultaneously interfere with multiple mechanisms in the infectious process.

It will be appreciated by one of skill in the art that any permutation or combination of anti-dengue antibodies in accordance with the present invention can be combined with any other antibody agent to formulate compositions and/or combination therapy regimens comprising a plurality of different anti-dengue antibodies.

Anti-dengue antibodies in accordance with the invention and pharmaceutical compositions thereof in accordance with the present invention may be administered according to any appropriate route and regimen. Preferably, a route or regimen is one that has been correlated with a positive therapeutic benefit. Preferably, a route or regimen is one that has been approved by the FDA and/or EP.

Preferably, the exact amount administered may vary from subject to subject, depending on one or more factors as is well known in the medical arts. Such factors may include, for example, one or more of species, age, general condition of the subject, severity of the infection, particular composition, its mode of administration, its mode of activity, the disorder being treated and the severity of the disorder; the activity of the specific anti-dengue antibody employed; the specific pharmaceutical composition administered; the half-life of the composition after administration; the age, body weight, general health, sex, and diet of the subject; the time of administration, route of administration, and rate of excretion of the specific compound employed; the duration of the treatment; drugs used in combination or coincidental with the specific compound employed and the like. Pharmaceutical compositions may be formulated in dosage unit form for ease of administration and uniformity of dosage. It will be understood, however, that the total daily usage of the compositions of the present invention will be decided by the attending physician within the scope of sound medical judgment.

Pharmaceutical compositions of the present invention may be administered by any route, as will be appreciated by those skilled in the art. Preferably, pharmaceutical compositions of the present invention are administered by oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical (e.g., by powders, ointments, creams, gels, lotions, and/or drops), mucosal, intranasal, buccal, enteral, vitreal, sublingual; by intratracheal instillation, bronchial instillation, and/or inhalation; as an oral spray, nasal spray, and/or aerosol, and/or through a portal vein catheter.

Preferably, anti-dengue antibodies in accordance with the present invention and/or pharmaceutical compositions thereof may be administered intravenously, for example, by intravenous infusion. Preferably, anti-dengue antibodies in accordance with the present invention and/or pharmaceutical compositions thereof may be administered by intramuscular injection. Preferably, anti-dengue antibodies in accordance with the present invention and/or pharmaceutical compositions thereof may be administered by subcutaneous injection. Preferably, anti-dengue antibodies in accordance with the present invention and/or pharmaceutical compositions thereof may be administered via portal vein catheter. However, the invention encompasses the delivery of DV anti-dengue antibodies in accordance with the present invention and/or pharmaceutical compositions thereof by any appropriate route taking into consideration likely advances in the sciences of drug delivery.

Preferably, anti-dengue antibodies in accordance with the present invention and/or pharmaceutical compositions thereof in accordance with the invention may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg of subject body weight per day to obtain the desired therapeutic effect. The desired dosage may be delivered more than three times per day, three times per day, two times per day, once per day, every other day, every third day, every week, every two weeks, every three weeks, every four weeks, every two months, every six months, or every twelve months. Preferably, the desired dosage may be delivered using multiple administrations (e.g., two, three, four, five, six, seven, eight, nine, ten, eleven, twelve, thirteen, fourteen, or more administrations).

Preferably, anti-dengue antibodies in accordance with the invention may be utilized for prophylactic applications. Preferably, prophylactic applications involve systems and methods for preventing, inhibiting progression of, and/or delaying the onset of DV infection, and/or any other DV-associated condition in individuals susceptible to and/or displaying symptoms of DV infection. Preferably, prophylactic applications involve systems and methods for preventing, inhibiting progression of, and/or delaying the onset of infection of the brain. Preferably, prophylactic applications involve systems and methods for preventing, inhibiting progression of, and/or delaying the impairment of vital organs (e.g., liver).

EXAMPLES

The present invention will be better understood in connection with the following Examples. However, it should be understood that these examples are for illustrative purposes only and are not meant to limit the scope of the invention. Various changes and modifications will be apparent to those skilled in the art and such changes and modifications including, without limitation, those relating to the formulations and/or methods of the invention may be made without departing from the spirit of the invention and the scope of the appended claims.

Example 1: Preparation of Recombinant NS1 Glycoprotein

Full-length NS1 protein from each of the dengue serotypes were obtained from a commercial source (Native Antigen Company, Oxfordshire, UK), using a mammalian expression system. Briefly, secreted NS1 was concentrated, purified using glass chromatography, and examined by SDS-PAGE under reducing conditions, with and without heat treatment. No heat treatment ensures that NS1 dimers can be observed by SDS-PAGE. The results demonstrated the presence of glycosylated monomers, glycosylated dimers and a small fraction of non-glycosylated monomers and non-glycosylated dimers.

Example 2: Preparation of Antibodies to NS1 Glycoprotein

Polyclonal mouse sera and monoclonal antibodies against the dengue NS1 glycoprotein isolated as described and in combination with a screening method were prepared generally as follows.

30 µg of purified NS1 in 50 µl of PBS was emulsified with equal volume of Complete Freund's Adjuvant and injected subcutaneously into a 5 week old female Balb/c mouse. Seven days later, the same amount of NS1 emulsified with Incomplete Freund's Adjuvant was injected intraperitoneally into the same mouse. The injection was repeated once more 21 days after the initial injection. On days 42, 43 and 46, the mouse received intraperitoneal injections of 30 μg of NS1 in 50 μl of PBS without adjuvant. Two days later the animal was sacrificed, and the spleen excised under sterile conditions.

The spleen was homogenized with scissors under serum free RPMI 1640 medium, and passed through a nylon cell strainer to form a splenocyte suspension. Splenocytes were collected by centrifugation, erythrocytes removed by Erythrocyte Lysis Reagent and washed with RPMI 1640. Mouse myeloma cells were grown in H-FSM medium, containing 5% FBS to a density of $4.3\times10^5$/ml. A total number of $5.6\times10^8$ myeloma cells, and separately splenocytes, were washed extensively by centrifugation with RPMI 1640 medium pre-warmed to 37° C. The myeloma cells and splenocytes were combined, centrifuged together, and the pellet was gently broken. Cell fusion was performed by adding polyethylene glycol (Mw 1,500) solution dropwise to the cell pellet at 37° C. The resulting cells were washed with RPMI 1640, resuspended in 300 ml of pre-warmed H-SFM 5% FBS, and distributed onto thirty 96-well cell culture plates, 100 μl of the cell suspension per well.

The cells were allowed to grow for a day, and were selected with 130 μl per well of the double concentration of HAT medium in H-SFM with FBS. Seven days later, 130 μl of each well content was removed, and replaced with similar, fresh medium, containing HAT at the recommended concentration.

Thirteen days after the cell fusion, culture supernatants of the resulting hybridoma lines were tested by a Pan NS1 ELISA. NS1s from each of the dengue serotypes were mixed in equal portions, the mix was coated onto ELISA plates (100 ng per well in 50 μl sodium carbonate/bicarbonate buffer pH 9.6) overnight at 4° C., and the wells were blocked with 200 μl per well of 5% nonfat dry milk in PBS containing 0.05% TWEEN™ 20 (ELISA Wash Buffer, EWB) for 1 hour at room temperature. After blocking, the wells were washed six times with EWB in an automated plate washer, and the hybridoma culture supernatants were incubated in the wells for 1 hour at room temperature. After another wash, the wells were incubated with goat antibodies specific for mouse immunoglobulin, labeled with horseradish peroxidase for 1 hour at room temperature, washed again and visualized with 3,3',5,5'-tetramethylbenzidine reagent. The reaction was stopped with 1 N sulfuric acid and read on an ELISA plate reader at 450 nm wavelength.

The hybridoma wells corresponding to positive ELISA results against a mix of the four serotypes of dengue NS1s were transferred into wells of a 96-well cell culture plate and grown in 1 ml of H-FSM/FBS medium, containing HT additive. The lines were repeatedly checked for specific antibody secretion and the supernatant form the positive wells were sequentially run in 4 individual ELISA tests, and the positive wells and the positive and negative individual results were reported. Form the list of clones, expansion, and re-testing was done using a FACS analysis of infected Vero cells with four different serotypes of dengue virus, individual clones were further expanded, cloned out by limiting dilution and cryopreserved in a final version of a "sub-cloned" hybridoma stable line.

Example 3: Sequencing of Antibodies Produced by Hybridomas

Total RNA was extracted from frozen hybridoma cells provided by the client and cDNA was synthesized from the RNA. PCR was then performed to amplify the variable regions (heavy and light chains) of the antibody, which were then cloned into a standard cloning vector separately and sequenced.

Materials

Hybridoma cells from hybridomas 724-55, 724-271, 724-323, 724-411, and 724-626.

TRIzol® Reagent (Ambion, Cat. No.: 15596-026);

PrimeScript™ 1st Strand cDNA Synthesis Kit (Takara, Cat. No.: 6110A).

Methods

Total RNA was isolated from the hybridoma cells following the technical manual of TRIzol® Reagent. The total RNA was analyzed by agarose gel electrophoresis. Total RNA was reverse transcribed into cDNA using isotype-specific anti-sense primers or universal primers following the technical manual of PrimeScript™ 1st Strand cDNA Synthesis Kit. The antibody fragments of VH and VL were amplified according to the standard procedures. Amplified antibody fragments were separately cloned into a standard cloning vector using standard molecular cloning procedures. Colony PCR screening was performed to identify clones with inserts of correct sizes. No less than five single colonies with inserts of correct sizes were sequenced for each antibody fragment.

Results and Analysis

The isolated total RNA of the sample was run alongside a DNA marker Marker III (TIANGEN), Cat. No.: MD103) on a 1.5% agarose/GelRed™ gel. Four microliters of PCR products of each sample were run alongside the DNA marker Marker III on a 1.5% agarose/GelRed™ gel. The PCR products were purified and stored at −20° C. until further use. Five single colonies with correct VH and VL insert sizes were sent for sequencing. The VH and VL genes of five different clones (see the attached file for sequence and sequence alignment for details) were found nearly identical.

The consensus sequence, of FIG. 18 is believed to be the sequence of the antibody produced by the hybridoma MA724-55. The consensus sequence, of FIG. 19, is believed to be the sequence of the antibody produced by the hybridoma MA724-271. The consensus sequence, of FIG. 20 is believed to be the sequence of the antibody produced by the hybridoma MA724-323. The consensus sequence, of FIG. 21 is believed to be the sequence of the antibody produced by the hybridoma MA724-411. The consensus sequence, of FIG. 22, is believed to be the sequence of the antibody produced by the hybridoma MA724-626.

Example 4: Characterization of Antibodies Raised Against NS1

Affinity purified antibodies were obtained by Protein L chromatography then resuspended in phosphate buffer and refrigerated until use. The conjugation of antibodies to the surface of gold nanoparticles was done following modified commercial antibody linking procedures (Innova, Inc). The conjugated antibodies were utilized in a lateral flow test or a half-strip test to find the optimal detection of the ligands by means of the intensity, presence or absence of a color signal on the surface of the strip.

The ability of the mAbs to make specific pairs for adaptation to a lateral flow detection of dengue infections was tested by using iterations of all the combinations possible and the combination with best binding capacity was selected as the preferable "pair" for conducting the test using a reference laboratory infection or a patient sample with known PCR positive serotype determination. In addition, the virus detected by PCR was fully sequenced to determine the geographical location worldwide of the isolate of virus being utilized. Samples from the Old World and New Worlds were equally detectable by the antibody pairs.

Isotypes of dengue-NS1-specific mAbs were evaluated by ELISA and by rapid tests obtained from a commercial source to define their IgG isotypes (IgG1, IgG2a, IgG2b).

Langmuir curves were generated to calculate an affinity constant for each antibody. Test line images were converted to gray scale, and then the intensity of the test line relative to the background was obtained using imaging software (NIH ImageJ). Test line intensities as a function of antigen concentration (c) are fit to the following equation:

$$\text{Intensity}=c/(K_d^{\textit{eff}} \times (1+(c/K_d^{\textit{eff}})))$$

resulting in a value for $K_d^{\textit{eff}}$, which is an effective dissociation constant and a measure of the affinity of the antibody for the antigen.

The low end sensitivity of this assay indicated that levels of 2 ng-20 ng were detectable in a half strip format. The $K_d^{\textit{eff}}$ calculations for antibody pairs 271/912 to bind to NS1 protein of serotype DV1 was found to be 1.099 nM. The $K_d^{eff}$ for the antibody pair 626/55 to bind to DV4 serotype NS1 protein was found to be 0.06742 nM. The numerical values for the sensitivity data is found in FIG. 26 and in Table 1 below.

TABLE 1

| Sensitivity Testing Numerical Values | | | | | |
|---|---|---|---|---|---|
| test | DENV1 | DENV2 | DEVN3 | DENV4 | DENV Pan |
| analysis | good | excellent | excellent | excellent | excellent |
| areas | 0.88 | 0.95 | 1.00 | 0.98 | 0.95 |
| Cut off | 1.14 | 1.18 | 1.20 | 1.37 | 1.19 |
| Sensitivity at cut off | 0.76 | 0.89 | 1.00 | 1.00 | 0.88 |
| Specificity at cut off | 0.89 | 0.98 | 1.00 | 0.96 | 1.00 |
| NUM. ALL positives | 17 | 9 | 16 | 6 | 58 |
| NUM. ALL negatives | 37 | 45 | 39 | 46 | 11 |
| NUM. true positives | 13 | 8 | 16 | 6 | 51 |
| NUM. true negatives | 33 | 44 | 39 | 44 | 11 |

TABLE 1-continued

| Sensitivity Testing Numerical Values | | | | | |
|---|---|---|---|---|---|
| test | DENV1 | DENV2 | DEVN3 | DENV4 | DENV Pan |
| NUM. false positives | 4 | 1 | 0 | 0 | 7 |
| NUM. false negatives | 4 | 1 | 0 | 2 | 0 |

Example 5: Epitope Comparison for NS1 Monoclonal Antibodies

An epitope binding assay was then performed to determine the binding to peptides immobilized in nitrocellulose, each peptide was provided by a non-profit repertoire of Biodefense reagents (ATCC distribution) indicated in Table 2 as BEI and after dilution in the appropriate buffer, each peptide was spotted at 10 μg using a manual pipettor. The antibodies were diluted and incubated with the matrix of peptides spotted onto the nitrocellulose and blocked in milk powder solution, similarly to conducting a Western Blot procedure, the final detection of the binding to each of the peptides spotted was accomplished by luminescence signal coming from a Horseradish Peroxidase conjugated secondary anti-mouse antibody and appropriate substrate solution and visualization of the membrane was done in a ChemiDoc instrument to generate a photographic output of the membrane. Since the matrix was composed with individual peptides spotted in specific locations, the number and identity of positive spots was recorded and reported as positive epitopes as shown in FIGS. 10-15 and FIGS. 24-26.

Example 6: NS1 Protein Alignment and Linear Epitope Mapping

NS1 protein alignment and linear epitope mapping of antibodies used in the dengue virus serotype-specific NS1 rapid tests and in the pan-dengue NS1 test were determined. The comparison of amino acid similarity was based on analyzing NS1 protein sequences from the following viruses: DENV1—Strain Singapore/5275/1990, accession number P33478; DENV2—Strain NGC, accession number AAA42941; DENV3-Philippines/H87/1956, accession number AAA99437; DENV4-Singapore/8976/1995, accession number AAV31422. Amino acid sequences were compared using an alignment software program, Color Align Conservation (Stothard P (2000) *The Sequence Manipulation Suite: JavaScript programs for analyzing and formatting protein and DNA sequences. Biotechniques* 28:1102-1104) to enhance the output of the sequence alignment program and the results are shown in FIG. 27. Residues that are identical among the sequences are given a black background, and those that are similar among the sequences are given a gray background. The remaining residues receive a white background. Linear peptide epitopes represented by antibodies 323, 1, 55, 912, 243, and 626 are shown in Table 2. The left column of Table 2 shows the antibody number, and the center column shows the use of the antibodies in the rapid tests. The right column shows linear epitopes in the viral NS1 proteins that were defined experimentally.

TABLE 2

Epitopes recognized by Antibodies Tested

| mAb # | IMMUNOCHROMATOGRAPHY APPLICATION | LINEAR EPITOPE |
|---|---|---|
| 271 | membrane, dipstick 1 (DENV serotype 1) nanoparticles, dipstick 5 (pan-DENV) | DV3 NS1: MELKYSWKTWGLAKIVT (SEQ ID NO: 2) [BEI] |
| 912 | nanoparticles, dipstick 1 (DENV serotype 1) | DV1 NS1 YGGPISQHNYR (SEQ ID NO: 33) |
| 1 | membrane, dipstick 2 (DENV serotype2) | DV1 NS1: MIRPQPMEHKYSWKS (SEQ ID NO: 34) DV1 NS1: HKYSWKSWGKAKIIG (SEQ ID NO: 35) |
| 243 | nanoparticles, dipstick 2 (DENV serotype 2) nanoparticles, dipstick 5 (pan-DENV) | DV2 NS1: GGPVSQHNYR (SEQ ID NO: 36) |
| 55 | membrane, dipstick 3 (DENV serotype 3) | DV3 NS1: MELKYSWKTWGLAKIVT (SEQ ID NO: 2) [BEI] DV3.NS1: GVFTTNIWLKLREVYTQ (SEQ ID NO: 3) [BEI] DV3.NS1: VEDYGFGVFTTNIWLKL (SEQ ID NO: 4) [BEI] DV4.NS1: GFGMFTTNIWMKFREG SEQ ID NO: 5) [BEI] |
| 411 | nanoparticles, dipstick 3 (DENV serotype 3) nanoparticles, dipstick 5 (pan-DENV) | DV3 NS1: MELKYSWKTWGLAKIVT SEQ ID NO: 2) [BEI] DV1 NS1: IWLKLRDSYTQMCDH (SEQ ID NO: 37) |
| 55 | membrane, dipstick 4 (DENV serotype 4) | DV3 NS1: MELKYSWKTWGLAKIVT (SEQ ID NO: 2) [BEI] DV3 NS1: GVFTTNIWLKLREVYTQ (SEQ ID NO: 3) [BEI] DV3 NS1: VEDYGFGVFTTNIWLKL (SEQ ID NO: 4) [BEI] DV4 NS1: GFGMFTTNIWMKFREG (SEQ ID NO: 5) |
| 626 | membrane, dipstick 4 (DENV serotype 4) nanoparticles, dipstick 5 (pan-DENV) | DV3 NS1: MELKYSWKTWGLAKIVT (SEQ ID NO: 2) [BEI] DV4 NS1: GFGMFTTNIWMKFREG (SEQ ID NO: 5) [BEI] |
| 323 | membrane, dipstick 5 (pan-DENV) | DV2.p15: TELKYSWKTWGKAKML (SEQ ID NO: 28) [BEI] DV3.p20: MELKYSWKTWGLAKIVT (SEQ ID NO: 2) [BEI] DV3.p29: GVFTTNIWLKLREVYTQ (SEQ ID NO: 3) [BEI] DV4.p20: PVNDLKYSWKTWGKAKI (SEQ ID NO; 1) [BEI] |

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the preferred embodiments described herein are not mutually exclusive and that features from the various preferred embodiments may be combined in whole or in part in accordance with the invention.

What is claimed is:

1. A diagnostic kit comprising at least one matched antibody pair that specifically bind and detect no more than one dengue virus NS1 protein serotype present in a biological sample wherein the at least one matched antibody pair is selected from the following pairs of monoclonal antibodies:

i) an antibody or antigen binding fragment thereof comprising a heavy chain variable region and a light chain variable region, wherein the heavy chain variable region comprises CDR1, CDR2, and CDR3 of SEQ ID NO: 21 and a light chain variable region comprises CDR1, CDR2 and CDR3 of SEQ ID NO: 23 and an antibody or antigen binding fragment thereof comprising a heavy chain variable region and a light chain variable region, wherein the heavy chain variable region comprises CDR1, CDR2 and CDR3 of SEQ ID NO: 25 and the light chain variable region comprises CDR1, CDR2 and CDR3 of SEQ ID NO: 27; and ii) an antibody or antigen binding fragment thereof comprising a heavy chain variable region and a light chain variable region, wherein the heavy chain variable region comprises CDR1, CDR2 and CDR3 of SEQ ID NO: 13 and the light chain variable region comprises CDR1, CDR2 and CDR3 of SEQ ID NO: 15 and an antibody or antigen binding fragment thereof comprising a heavy chain variable region and a light chain variable region, wherein the heavy chain variable region comprises CDR1, CDR2 and CDR3 of SEQ ID NO: 17 and the light chain variable region comprises CDR1, CDR2 and CDR3 of SEQ ID NO: 19.

2. The diagnostic kit of claim 1, wherein the matched antibody pair will not detect any protein from Zika virus present in the biological sample.

3. The diagnostic kit of claim 1, wherein at least one antibody of each antibody pair comprises a detection label.

4. The diagnostic kit of claim 3, wherein the detection label is selected from biotin, avidin, gold nanoparticles, colored latex beads, magnetic particles, carbon nanoparticles, selenium nanoparticles, silver nanoparticles, quantum dots, up converting phosphors, organic fluorophores, textile dyes, enzymes, and liposomes.

5. The diagnostic kit of claim 1, wherein the matched antibody pair does not detect yellow fever virus in a sample.

6. The diagnostic kit of claim 1, further comprising an enzyme-linked immunosorbent assay (ELISA) kit.

7. The diagnostic kit of claim 6, wherein the ELISA is a sandwich ELISA.

* * * * *